United States Patent
Sambursky et al.

(10) Patent No.: US 9,939,434 B2
(45) Date of Patent: *Apr. 10, 2018

(54) MULTIPLANAR LATERAL FLOW ASSAY WITH SAMPLE COMPRESSOR

(71) Applicant: Rapid Pathogen Screening, Inc., Sarasota, FL (US)

(72) Inventors: Robert P. Sambursky, Bradenton, FL (US); Uma Mahesh Babu, Bradenton, FL (US); Robert W. VanDine, Montoursville, PA (US); Ganga V. Kanaujia, San Antonio, TX (US); Thomas Orsini, Sarasota, FL (US)

(73) Assignee: Rapid Pathogen Screening, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,602

(22) Filed: Mar. 17, 2014

(65) Prior Publication Data

US 2014/0199710 A1 Jul. 17, 2014

Related U.S. Application Data

(62) Division of application No. 13/796,736, filed on Mar. 12, 2013, now abandoned, which is a division of
(Continued)

(51) Int. Cl.
*G01N 33/543* (2006.01)
*G01N 33/53* (2006.01)
(Continued)

(52) U.S. Cl.
CPC ...... *G01N 33/54306* (2013.01); *B01L 3/5023* (2013.01); *G01N 33/5302* (2013.01);
(Continued)

(58) Field of Classification Search
CPC ............ G01N 33/54306; G01N 33/5302
See application file for complete search history.

(56) References Cited

U.S. PATENT DOCUMENTS

| 4,299,916 A | 11/1981 | Litman et al. |
| 4,405,711 A | 9/1983 | Masuda et al. |
(Continued)

FOREIGN PATENT DOCUMENTS

| DE | 19622503 | 7/1998 |
| EP | 306772 A1 | 3/1989 |
(Continued)

OTHER PUBLICATIONS

Barnard, et al., "Development of an Oligonucleotide-Based SNP Detection Method on Lateral Flow Strips Using Hexapet Tags," Point of Care, vol. 4, No. 3, pp. 108-118 (Sep. 2005).
(Continued)

*Primary Examiner* — Scott Long
*Assistant Examiner* — Gary E Hollinden
(74) *Attorney, Agent, or Firm* — Brown & Michaels, PC

(57) ABSTRACT

A sample compressor applies pressure to a sample collector and a sample application zone of a test strip to transfer a sample from the sample collector and a binding partner of an analyte to the sample application zone in a lateral flow device. At least one of the binding partners of the analyte is not located on the test strip prior to use of the lateral flow device. The test strip may be a universal test strip with no molecule that specifically binds the analyte is located on the test strip. The sample compressor may be a universal sample compressor also with no molecule that specifically binds the analyte on the sample compressor. The lateral flow device may also include one or more enhancement elements, where the enhancement elements bind to the analyte sandwich to increase a detection signal in the test zone.

18 Claims, 19 Drawing Sheets

Related U.S. Application Data application No. 12/958,454, filed on Dec. 2, 2010, now Pat. No. 8,609,433.

(60) Provisional application No. 61/266,641, filed on Dec. 4, 2009, provisional application No. 61/331,966, filed on May 6, 2010, provisional application No. 61/352,093, filed on Jun. 7, 2010, provisional application No. 61/392,981, filed on Oct. 14, 2010.

(51) Int. Cl.
*B01L 3/00* (2006.01)
*G01N 33/558* (2006.01)

(52) U.S. Cl.
CPC ......... *G01N 33/543* (2013.01); *G01N 33/558* (2013.01); *B01L 3/502715* (2013.01); *B01L 3/502738* (2013.01); *B01L 2200/027* (2013.01); *B01L 2400/0633* (2013.01); *Y10T 436/25* (2015.01)

(56) References Cited

U.S. PATENT DOCUMENTS

| | | | |
|---|---|---|---|
| 4,429,050 A | 1/1984 | Yasuda et al. |
| 4,473,652 A | 9/1984 | Okazaki et al. |
| 4,508,820 A | 4/1985 | Merril et al. |
| 4,554,254 A | 11/1985 | Krystal |
| 4,703,016 A | 10/1987 | Merril |
| 4,861,711 A | 8/1989 | Friesen et al. |
| 4,920,046 A | 4/1990 | McFarland et al. |
| 4,956,302 A | 9/1990 | Gordon et al. |
| 4,960,691 A | 10/1990 | Gordon et al. |
| 4,960,692 A | 10/1990 | Lentrichia et al. |
| 4,963,325 A | 10/1990 | Lennon et al. |
| 4,981,786 A | 1/1991 | Dafforn et al. |
| 5,026,653 A | 6/1991 | Lee et al. |
| 5,084,245 A | 1/1992 | Berke et al. |
| 5,120,643 A | 6/1992 | Ching et al. |
| 5,212,065 A | 5/1993 | Pegg et al. |
| 5,221,678 A | 6/1993 | Atkinson et al. |
| 5,312,921 A | 5/1994 | Glazer et al. |
| 5,348,891 A | 9/1994 | van Es et al. |
| 5,405,430 A | 4/1995 | Groves et al. |
| 5,436,134 A | 7/1995 | Haugland et al. |
| 5,482,830 A | 1/1996 | Bogart et al. |
| 5,496,562 A | 3/1996 | Burgoyne |
| 5,607,863 A | 3/1997 | Chandler |
| 5,637,469 A | 6/1997 | Wilding et al. |
| 5,658,751 A | 8/1997 | Yue et al. |
| 5,695,949 A | 12/1997 | Galen et al. |
| 5,705,353 A | 1/1998 | Oh et al. |
| 5,714,341 A | 2/1998 | Thieme et al. |
| 5,756,126 A | 5/1998 | Burgoyne |
| 5,763,162 A | 6/1998 | Glazer et al. |
| 5,783,687 A | 7/1998 | Glazer et al. |
| 5,807,527 A | 9/1998 | Burgoyne |
| 5,824,268 A | 10/1998 | Bernstein et al. |
| 5,863,740 A | 1/1999 | Kientsch-Engel et al. |
| 5,869,345 A | 2/1999 | Chandler |
| 5,877,028 A | 3/1999 | Chandler et al. |
| 5,888,778 A | 3/1999 | Shuber |
| 5,939,252 A | 8/1999 | Lennon et al. |
| 5,945,345 A | 8/1999 | Blatt et al. |
| 5,972,386 A | 10/1999 | Burgoyne |
| 5,985,327 A | 11/1999 | Burgoyne |
| 5,985,675 A | 11/1999 | Charm et al. |
| 5,989,813 A | 11/1999 | Gerdes |
| 5,998,220 A | 12/1999 | Chandler |
| 6,002,734 A | 12/1999 | Steinman |
| 6,017,767 A | 1/2000 | Chandler |
| 6,037,127 A | 3/2000 | Ebersole et al. |
| 6,046,058 A | 4/2000 | Sun |
| 6,054,272 A | 4/2000 | Glazer et al. |
| 6,060,237 A | 5/2000 | Nygren et al. |
| 6,087,184 A | 7/2000 | Magginetti et al. |
| 6,106,779 A | 8/2000 | Buechler et al. |
| 6,136,610 A | 10/2000 | Polito et al. |
| 6,146,589 A | 11/2000 | Chandler |
| 6,225,046 B1 | 5/2001 | Vesey et al. |
| 6,235,539 B1 | 5/2001 | Carpenter |
| 6,284,550 B1 | 9/2001 | Carroll et al. |
| 6,335,205 B1 | 1/2002 | Bausback |
| 6,350,578 B1 | 2/2002 | Stark et al. |
| 6,355,429 B1 | 3/2002 | Nygren et al. |
| 6,358,752 B1 | 3/2002 | Durst et al. |
| 6,514,773 B1 | 2/2003 | Klein et al. |
| 6,548,309 B1 | 4/2003 | Moore et al. |
| 6,555,390 B2 | 4/2003 | Chandler |
| 6,565,808 B2 | 5/2003 | Hudak et al. |
| 6,566,101 B1 | 5/2003 | Shuber et al. |
| 6,569,627 B2 | 5/2003 | Wittwer et al. |
| 6,602,669 B2 | 8/2003 | Letsinger et al. |
| 6,703,196 B1 | 3/2004 | Klepp et al. |
| 6,783,938 B2 | 8/2004 | Nygren et al. |
| 6,875,619 B2 | 4/2005 | Blackburn |
| 6,893,880 B2 | 5/2005 | Carpenter |
| 6,902,900 B2 | 6/2005 | Davies et al. |
| 7,189,522 B2 | 3/2007 | Esfandiari |
| 7,267,992 B2 | 9/2007 | Goerlach-Graw et al. |
| 7,309,611 B2 | 12/2007 | DiNello et al. |
| 7,314,763 B2 | 1/2008 | Song et al. |
| 7,341,837 B2 | 3/2008 | Lawton |
| 7,354,614 B2 | 4/2008 | Quinlan et al. |
| 7,371,582 B2 | 5/2008 | Nahm et al. |
| 7,374,950 B2 | 5/2008 | Kang et al. |
| 7,384,598 B2 | 6/2008 | Quirk et al. |
| 7,393,697 B2 | 7/2008 | Charlton |
| 7,425,302 B2 | 9/2008 | Piasio et al. |
| 7,459,314 B2 | 12/2008 | Guo et al. |
| 7,583,379 B2 | 9/2009 | Zhao et al. |
| 7,704,729 B2 | 4/2010 | Chandler |
| 7,723,124 B2 | 5/2010 | Aberl et al. |
| 7,732,132 B2 | 6/2010 | Huang et al. |
| 7,736,890 B2 | 6/2010 | Sia et al. |
| 7,741,103 B2 | 6/2010 | Guirguis |
| 7,910,381 B2 | 3/2011 | Ford et al. |
| 8,383,422 B2 | 2/2013 | Katada et al. |
| 8,647,574 B2 | 2/2014 | Halverson et al. |
| 8,877,515 B2 | 11/2014 | Chiku et al. |
| 9,101,927 B2 * | 8/2015 | Alajem ................ B01L 3/5023 |
| 2002/0146844 A1 | 10/2002 | Pronovost et al. |
| 2003/0049658 A1 | 3/2003 | Smart et al. |
| 2003/0073121 A1 | 4/2003 | Mendel-Hartvig et al. |
| 2003/0104506 A1 | 6/2003 | Durst et al. |
| 2003/0108940 A1 | 6/2003 | Inoko et al. |
| 2003/0166291 A1 | 9/2003 | Jones et al. |
| 2003/0186463 A1 | 10/2003 | Hudak et al. |
| 2003/0190681 A1 | 10/2003 | Shai |
| 2004/0101889 A1 | 5/2004 | Letsinger et al. |
| 2004/0110167 A1 | 6/2004 | Gerdes et al. |
| 2004/0152142 A1 | 8/2004 | Klepp et al. |
| 2004/0156037 A1 | 8/2004 | Mawhirt et al. |
| 2004/0241779 A1 | 12/2004 | Piasio et al. |
| 2005/0032244 A1 | 2/2005 | Nie et al. |
| 2005/0147532 A1 | 7/2005 | Bellet et al. |
| 2005/0164305 A1 | 7/2005 | Golz et al. |
| 2005/0181517 A1 | 8/2005 | Chandler et al. |
| 2005/0191704 A1 * | 9/2005 | Boga .................. G01N 33/523 435/7.1 |
| 2005/0227223 A1 | 10/2005 | Miyawaki |
| 2005/0227275 A1 | 10/2005 | Jung et al. |
| 2005/0239056 A1 | 10/2005 | Piasio et al. |
| 2006/0003390 A1 | 1/2006 | Schaffler et al. |
| 2006/0019406 A1 | 1/2006 | Wei et al. |
| 2006/0024843 A1 | 2/2006 | Lee et al. |
| 2006/0057608 A1 | 3/2006 | Kaufman |
| 2006/0110285 A1 | 5/2006 | Piasio et al. |
| 2006/0147927 A1 | 7/2006 | Geddes et al. |
| 2006/0160078 A1 | 7/2006 | Cardy et al. |
| 2006/0172434 A1 | 8/2006 | Rowell |
| 2006/0199278 A1 | 9/2006 | Leclipteux et al. |
| 2006/0216704 A1 | 9/2006 | Newton et al. |
| 2006/0223192 A1 | 10/2006 | Smith et al. |

(56) References Cited

U.S. PATENT DOCUMENTS

| | | |
|---|---|---|
| 2006/0240569 A1 | 10/2006 | Goldenbaum et al. |
| 2006/0246601 A1* | 11/2006 | Song ............... G01N 33/54366 436/514 |
| 2006/0263907 A1 | 11/2006 | Zweig |
| 2007/0003992 A1 | 1/2007 | Pentyala |
| 2007/0015290 A1 | 1/2007 | Raj |
| 2007/0048807 A1* | 3/2007 | Song ................... G01N 33/521 435/7.5 |
| 2007/0059682 A1 | 3/2007 | Aberl et al. |
| 2007/0141564 A1 | 6/2007 | Aberl et al. |
| 2007/0184506 A1 | 8/2007 | Klepp |
| 2007/0202497 A1 | 8/2007 | Renuart et al. |
| 2007/0224701 A1 | 9/2007 | Rosenstein |
| 2007/0264629 A1 | 11/2007 | Holmes et al. |
| 2008/0003141 A1 | 1/2008 | Iketani |
| 2008/0032319 A1 | 2/2008 | Nam |
| 2008/0085525 A1 | 4/2008 | Van Herwijnen |
| 2008/0102473 A1 | 5/2008 | Fouquet et al. |
| 2008/0194041 A1 | 8/2008 | Guirguis |
| 2008/0199851 A1 | 8/2008 | Egan et al. |
| 2008/0310998 A1 | 12/2008 | Lamotte |
| 2008/0318341 A1 | 12/2008 | Esfandiari |
| 2009/0011436 A1 | 1/2009 | Piasio et al. |
| 2009/0047673 A1 | 2/2009 | Cary |
| 2009/0155811 A1 | 6/2009 | Natan et al. |
| 2009/0232702 A1 | 9/2009 | Wu et al. |
| 2009/0289201 A1 | 11/2009 | Babu et al. |
| 2009/0291508 A1 | 11/2009 | Babu et al. |
| 2009/0305231 A1 | 12/2009 | Weidemaier et al. |
| 2009/0305290 A1 | 12/2009 | Sambursky et al. |
| 2010/0015634 A1 | 1/2010 | VanDine et al. |
| 2010/0112725 A1 | 5/2010 | Babu et al. |
| 2010/0143891 A1 | 6/2010 | Aberl et al. |
| 2010/0143941 A1 | 6/2010 | Wu et al. |
| 2010/0209297 A1 | 8/2010 | Raj et al. |
| 2010/0279310 A1 | 11/2010 | Sia et al. |
| 2010/0291536 A1 | 11/2010 | Viljoen et al. |
| 2010/0297611 A1 | 11/2010 | Sambursky et al. |
| 2011/0027908 A1 | 2/2011 | Siciliano et al. |

FOREIGN PATENT DOCUMENTS

| | | |
|---|---|---|
| EP | 582231 A1 | 2/1994 |
| EP | 1489416 A1 | 12/2004 |
| JP | 2007114097 A | 5/2007 |
| WO | 9960402 A1 | 11/1999 |
| WO | 3073817 A2 | 9/2003 |
| WO | 2007063326 A2 | 6/2007 |
| WO | 2007070117 A1 | 6/2007 |
| WO | 2007110779 A2 | 10/2007 |
| WO | 2007123507 A1 | 11/2007 |
| WO | 2008014709 A1 | 2/2008 |
| WO | 2009044167 A1 | 4/2009 |

OTHER PUBLICATIONS

Berezovski, et al. "Cell lysis inside the capillary facilitated by transverse diffusion of laminar flow profiles (TDLFP)," Anal Bioanal Chem (2007) 387:91-96.

Bruning et al., "A rapid chromatographic strip test for the pen-side diagnosis of rinderpest virus," Journal of Virological Methods 81 (1999) 143-154.

Chieux V, et al., "The MxA protein levels in whole blood lysates of patients with various viral infections," Journal of Virological Methods 70 (1998) 183-191.

Choi, et al., "A rapid, simple measurement of human albumin in whole blood using a fluorescence immunoassay (I)," Clinica Chimica Acta 339 (2004) 147-156.

Dineva et al., "Simultaneous Visual Detection of Multiple Viral Amplicons by Dipstick Assay", Journal of Clinical Microbiology, Aug. 2005, p. 4015-4021.

Extended European Search Report dated Apr. 17, 2013. European Application No. 10835165.1 (PCT/US2010058827).

FTA Nucleic Acid Collection, Storage and Purification, http://whatman.com/products.aspx?PID=108, 2007.

International Search Report and Written Opinion dated Feb. 18, 2010, International Application No. PCT/US2009/050645.

International Search Report and Written Opinion dated Jan. 22, 2010, International Application No. PCT/US2009/046848.

International Search Report and Written Opinion dated Mar. 12, 2010, International Application No. PCT/US2009/050653.

International Search Report and Written Opinion for International Application No. PCT/US2010/058827 dated Nov. 30, 2011.

Karle, et al., "Application of FTA-based Technology for Sample Collection, Transport, Purification, and Storage of PCR-ready Plant DNA" (Nov. 2003).

O'Mahony, et al., "Integration of Bacteria Capture via Filtration and in Situ Lysis for Recovery of Plasmid DNA under Industry-Compatible Conditions," Biotechnol. Prog. 2007, 23, 895-903.

Parida M.M., "Rapid and real-time detection technologies for emerging viruses of biomedical importance," J. Biosci. 33(4), Nov. 2008, 617-628.

Sambursky et al., "The RPS Adeno Detector for Diagnosing Adenoviral Conjunctivitis," Ophthalmology 2006; 113:1758-1764.

Sambursky, "510-K Summary of Safety and Effectiveness" (Sep. 14, 2005).

Uchio, et al., Rapid Diagnosis of Adenoviral Conjunctivitis on Conjunctival.

Udeh et al., Cost Effectiveness of a Point-of-Care Test for Adenoviral.

* cited by examiner

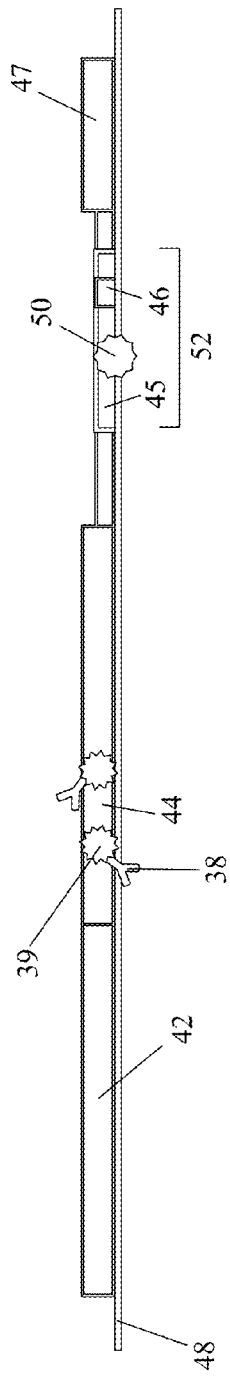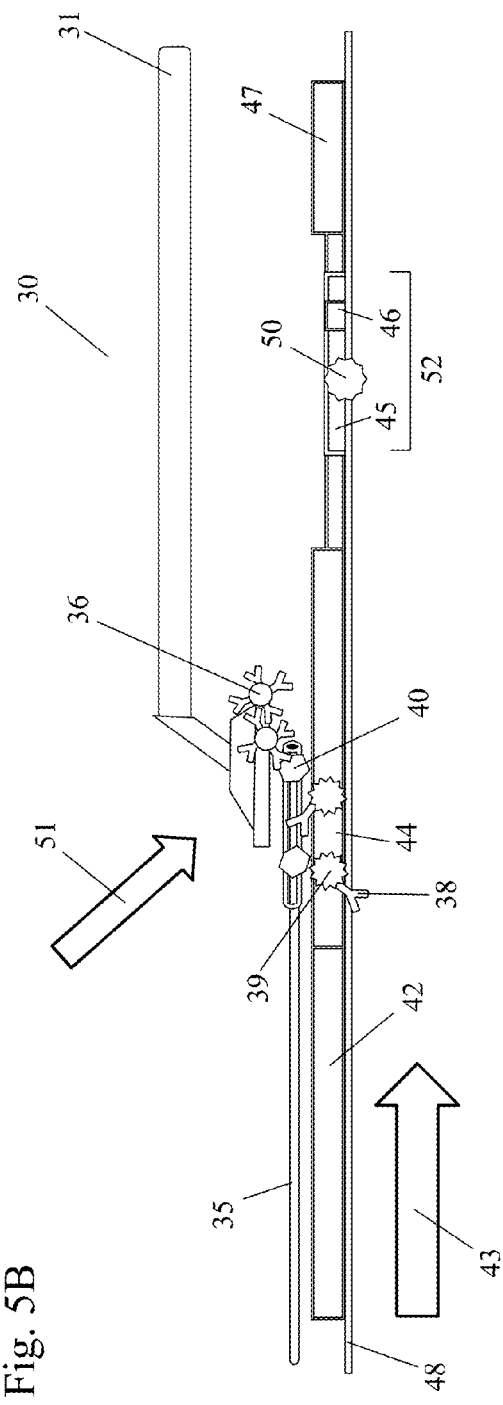

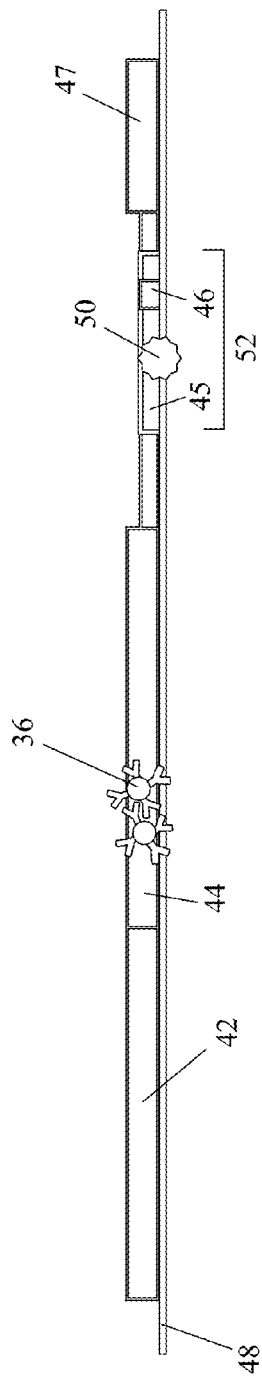
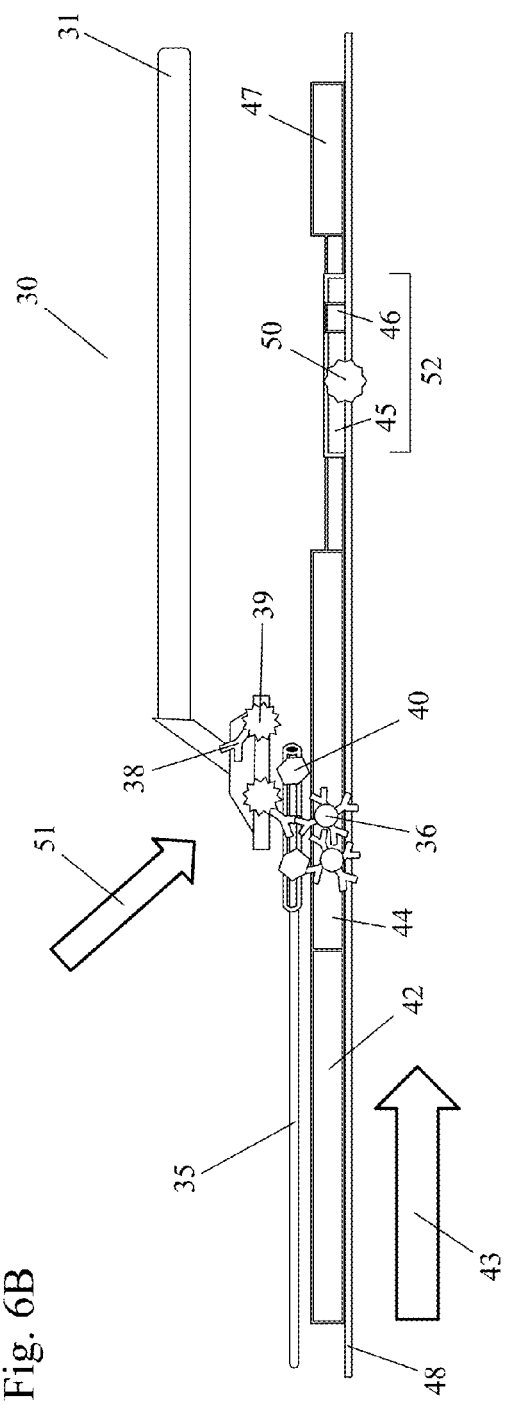
Fig. 6A
Fig. 6B

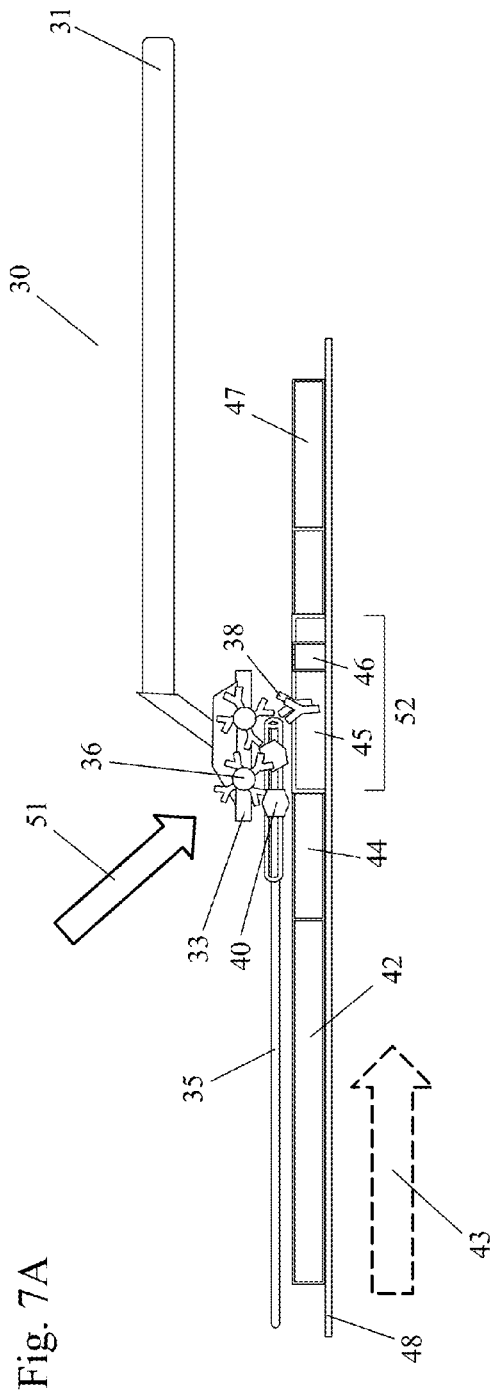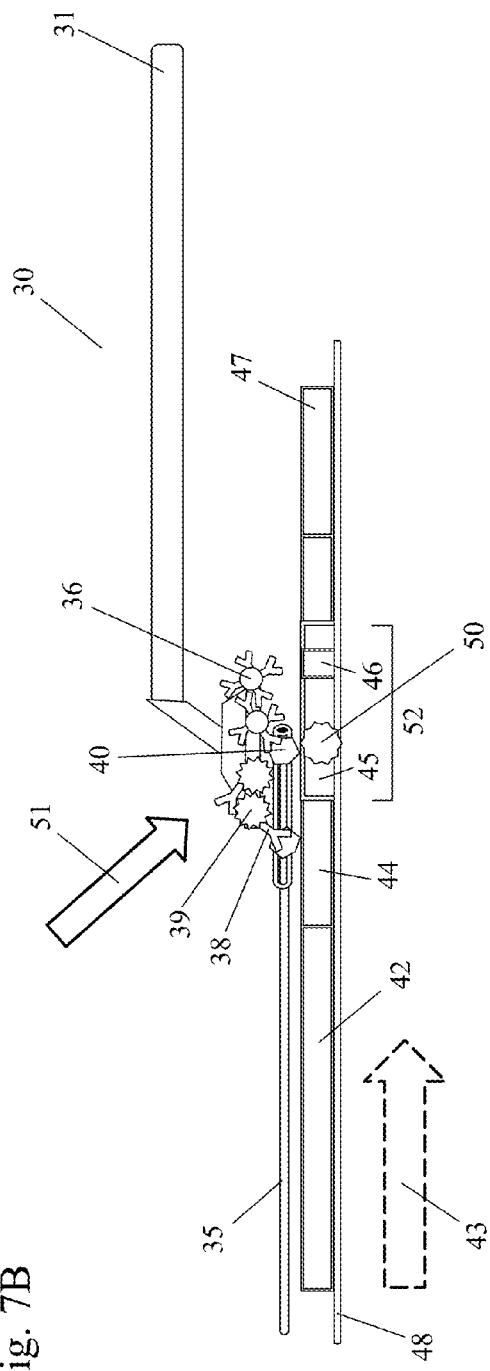

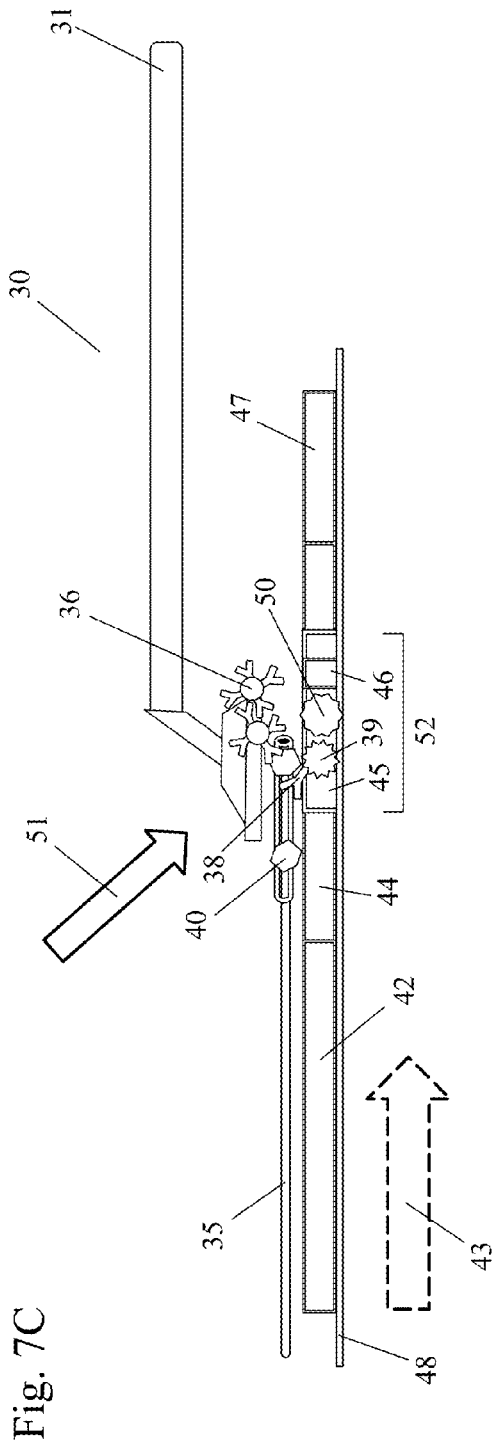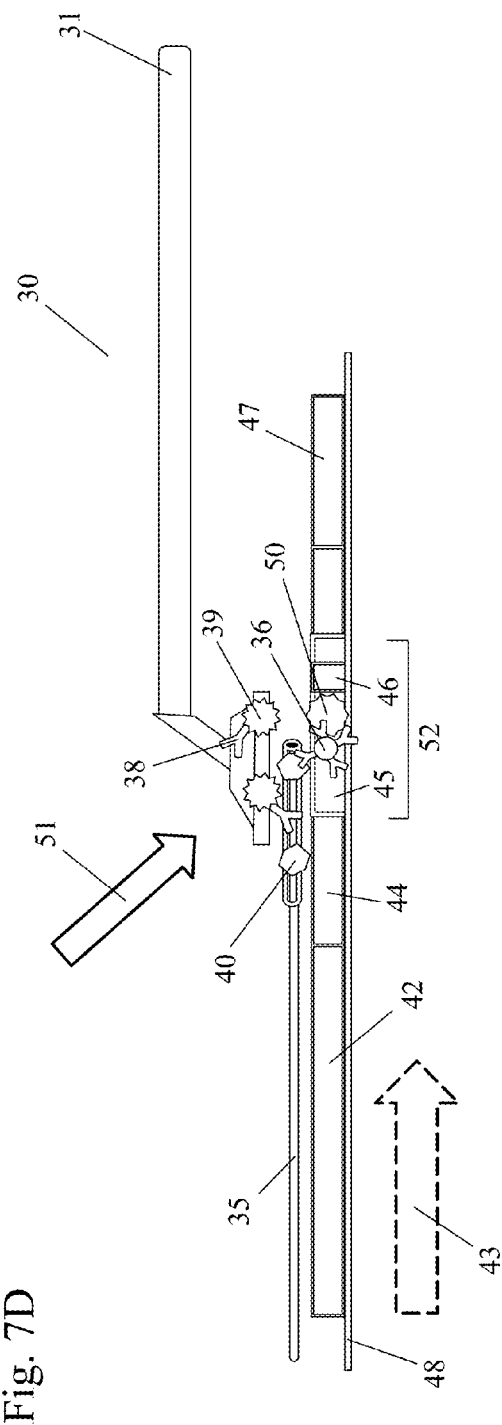

MULTIPLANAR LATERAL FLOW ASSAY WITH SAMPLE COMPRESSOR

REFERENCE TO RELATED APPLICATIONS

This is a divisional patent application of copending application Ser. No. 13/796,736, filed Mar. 12, 2013, entitled "MULTIPLANAR LATERAL FLOW ASSAY WITH SAMPLE COMPRESSOR", which is a divisional application of application Ser. No. 12/958,454, filed Dec. 2, 2010, entitled "MULTIPLANAR LATERAL FLOW ASSAY WITH SAMPLE COMPRESSOR", now issued U.S. Pat. No. 8,609,433, issued Dec. 17, 2013, which claims one or more inventions which were disclosed in Provisional Application No. 61/266,641, filed Dec. 4, 2009, entitled "LATERAL FLOW NUCLEIC ACID DETECTOR", Provisional Application No. 61/331,966, filed May 6, 2010, entitled "MULTIPLANAR LATERAL FLOW ASSAY WITH SAMPLE COMPRESSOR", Provisional Application No. 61/352,093, filed Jun. 7, 2010, entitled "LATERAL FLOW ASSAYS", and Provisional Application No. 61/392,981, filed Oct. 14, 2010, entitled "MULTIPLANAR LATERAL FLOW ASSAY WITH SAMPLE COMPRESSOR". The benefit under 35 USC § 119(e) of the United States provisional applications is hereby claimed, and the aforementioned applications are hereby incorporated herein by reference.

BACKGROUND OF THE INVENTION

Field of the Invention

The invention pertains to the field of point of care tests. More particularly, the invention pertains to lateral flow assays.

Description of Related Art

Lateral flow assays are a subset of assays combining various reagents and process steps in one assay strip, thus providing a sensitive and rapid means for the detection of target molecules. Antibody-based lateral flow immunoassays are available for a wide range of target analytes and can be designed for sandwich or competitive test principles. Generally, high molecular weight analytes with several epitopes are analyzed in a sandwich format whereas small molecules representing only one epitope are detected by means of a competitive assay. The first tests were made for human chorionic gonadotropin (hCG). Today there are commercially available tests for monitoring ovulation, detecting infectious disease organisms, analyzing drugs of abuse, and measuring other analytes important to human physiology. Products have also been introduced for veterinary testing, environmental testing, and product monitoring.

In the prior art, the mobile labeled receptor (also known as the tracer or the test conjugate herein) in these assays is either dried on the test strip, contained in an external eluting solution (such that it can be pre-mixed with the sample prior to application on the test strip), or part of the elution media.

European patent publication EP0582231, published Feb. 9, 1994, entitled "SOLID PHASE ASSAY", discloses an assay with a porous solid support with a first portion that contacts a sample that may include an analyte of interest. The sample flows through the solid support, and the analyte, if present, combines with a tracer, which is reversibly bound on the solid support. The sample and the tracer initially travel in a direction perpendicular to the first portion (e.g. vertically) via capillary flow. The tracer and analyte then continue to travel by capillary flow through the material to a second portion that includes an immobilized binder, which binds to the analyte in a sandwich immunoassay format. Travel to the second portion occurs in a direction perpendicular to the direction in which the tracer and sample initially travel (e.g. laterally). All travel of the sample and tracer occur due to capillary flow through the device. Although travel occurs vertically and laterally, there is a single flow path. The sample, the tracer, and the immobilized binder are all in the same flow path.

U.S. Patent Publication No. 2007/0224701, published Sep. 27, 2007, entitled "COMBINATION VERTICAL AND LATERAL FLOW IMMUNOASSAY DEVICE", discloses immunoassay devices, kits, and methods for determining the presence or absence of an analyte in a liquid sample using a combination of vertical flow and lateral flow. The device includes a tracer pad with a labeled receptor that is vertically juxtaposed with a binder support medium. The device disclosed in this publication is multi-sectioned, but, similar to EP0582231, only has a single flow path. The sample, the labeled receptor, and the binder support medium are all in the same flow path.

SUMMARY OF THE INVENTION

A sample compressor applies pressure to a sample collector at the sample application zone of a test strip to transfer a sample on the sample collector and a binding partner of an analyte to the sample application zone in a lateral flow device. At least one of the binding partners of the analyte is not located on the test strip or in the eluting solution prior to use of the lateral flow device. The test strip may be a universal test strip with no molecule that specifically binds the analyte on the test strip. The sample compressor may be a universal sample compressor with no molecule that specifically binds the analyte on the sample compressor. The lateral flow device may also include an enhancement element, where the enhancement element binds to the analyte sandwich to increase a detection signal in the test zone.

In one embodiment of the present invention, the lateral flow device for detecting an analyte includes a sample compressor, a sample collector with a sample collection portion, a test strip with a sample application zone and a test zone, a conjugate including a first binding partner for the analyte and a label, and a second binding partner for the analyte. Either the conjugate or the second binding partner or both the conjugate and the second binding partner are not located on the test strip prior to use of the lateral flow device. The sample compressor, the sample collector, and the test strip form a vertical stack to apply the sample to the test strip by compression. The sample compressor preferably has a pad/fleece with the conjugate and/or the second binding partner being located on the pad prior to use of the lateral flow device. In some embodiments, the lateral flow device includes a first control binding partner located on the sample compressor pad and a second control binding partner immobilized in a control zone of the test strip, where the first control binding partner is a binding partner for the second control binding partner. The lateral flow device is preferably formed such that a positive result is only achieved by isolation of the analyte in the test zone by binding of the analyte to the first binding partner and the second binding partner. The test zone preferably includes no molecule which specifically binds the analyte. Preferably, the second binding partner includes a tag and the test zone includes an immobilized binding partner for the tag.

In another embodiment of the present invention, the universal test strip includes a test zone but no molecule which specifically binds an analyte. The test strip preferably also includes a control zone with a control binding partner immobilized in the control zone. The test strip preferably also includes a tag immobilized in the test zone, where the tag is biotin, avidin, neutravidin, streptavidin, a lectin, or a glycosyl moiety.

In yet another embodiment of the present invention, the sample compressor for use in a lateral flow device includes a pad and at least one binding partner of an analyte. The sample compressor preferably also includes a mobile control binding partner on the pad.

In some embodiments, the sample compressor is a universal sample compressor with no molecule which specifically binds an analyte. The universal sample compressor preferably includes a pad and a mobile control binding partner on the pad.

In another embodiment of the present invention, the lateral flow device for detecting an analyte includes a test strip with a sample application zone and a test zone, a conjugate with a first binding partner for the analyte and a label, a second binding partner for the analyte, and an enhancement element. The analyte, the conjugate, and the second binding partner form a sandwich which is immobilized in the test zone when the analyte is present, and the enhancement element binds to the sandwich to increase a detection signal in the test zone. In some embodiments, the conjugate includes colloidal gold and the enhancement element includes at least one silver salt. In other embodiments, the enhancement element includes an antigen and the conjugate includes a specific binding partner for the antigen. The enhancement element preferably includes a label. In a preferred embodiment, the test zone does not include a molecule which specifically binds the analyte. Preferably, the second binding partner includes a tag and the test zone includes an immobilized binding partner of the tag.

In yet another embodiment of the present invention, the method of applying a sample to a test strip of a lateral flow device includes placing a sample collector with a sample collection portion with the sample in a vertical stack between a sample compressor and a sample application zone of the test strip and applying a pressure to the sample collection portion using the sample compressor to transfer at least a portion of the sample to the sample application zone. The method preferably includes placing a pad with a binding partner for an analyte on the vertical stack, and applying the pressure to transfer at least a portion of the binding partner to the sample application zone. Transfer of the sample to the sample application zone preferably does not occur by flow.

In yet another embodiment of the present invention, the method of applying a sample to a test strip of a lateral flow device includes first placing at least one external binding partner on the sample application zone of the test strip. The external binding partner may be located on an external pad. In embodiments where there are two analyte binding partners that bind the analyte prior to reaching the test zone, either one or both of the analyte binding partners may be added. A sample collector that includes the sample is placed in a vertical stack between the external binding partner and a sample compressor. The sample compressor applies pressure to the sample collector to transfer the external binding partner and at least a portion of the sample to the sample application zone. Alternatively, the external binding partner could be added and compressed by the sample compressor, then removed, before the sample collector is stacked above the sample application zone, where the sample is compressed onto the test strip. In another alternative embodiment, at least one external binding partner is placed in the vertical stack between the sample compressor and sample collector. Alternatively, the sample collector is added and compressed, then removed, and then the external binding partner is added and compressed onto the test strip. In other embodiments, the sample collector is in a vertical stack between a first external binding partner and a second external binding partner, and the sample compressor applies pressure to the vertical stack. In these embodiments, neither the strip nor the sample compressor has a specific analyte binding partner.

BRIEF DESCRIPTION OF THE DRAWINGS

FIG. 5A shows yet another lateral flow test strip in an embodiment of the present invention.

FIG. 5B shows a lateral flow device including the test strip of FIG. 5A, a sample collector, and a sample compressor in another embodiment of the present invention.

FIG. 6A shows another lateral flow test strip in an embodiment of the present invention.

FIG. 6B shows a lateral flow device including the test strip of FIG. 6A, a sample collector, and a sample compressor in another embodiment of the present invention.

FIG. 7A shows a device similar to the device of FIG. 3C except that the test zone is in the sample application zone in an embodiment of the present invention.

FIG. 7B shows a device similar to the device of FIG. 4C except that the test zone is in the sample application zone in an embodiment of the present invention.

FIG. 7C shows a device similar to the device of FIG. 5B except that the test zone is in the sample application zone in an embodiment of the present invention.

FIG. 7D shows a device similar to the device of FIG. 6B except that the test zone is in the sample application zone in an embodiment of the present invention.

DETAILED DESCRIPTION OF THE INVENTION

Figure 1:
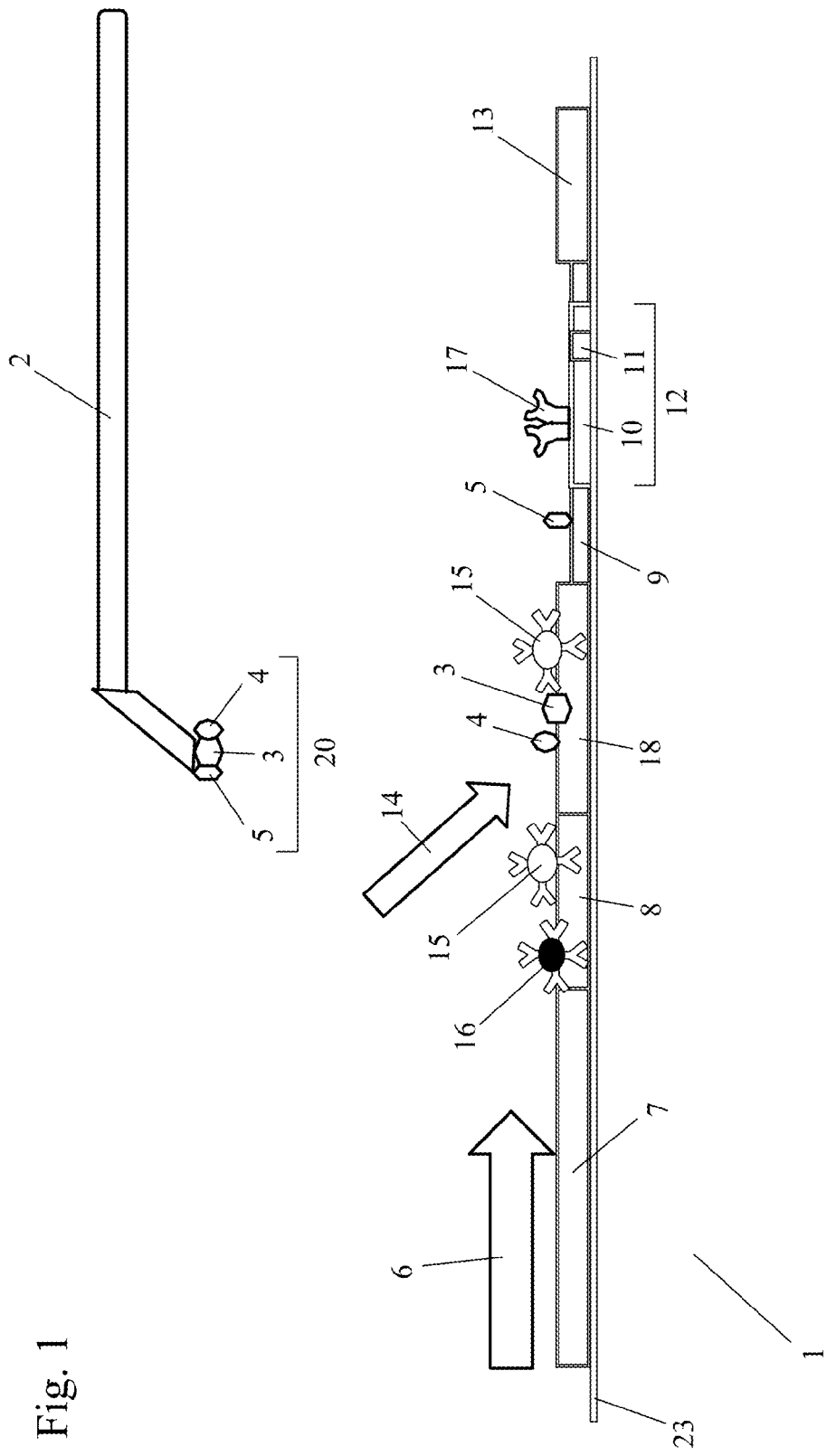
FIG. 1 shows a test strip and a sample collector in a lateral flow device.

The present invention relates to methods and devices for detecting an analyte (also known as the target) in a sample, where the sample to be analyzed is applied to a chromatographic carrier. In multi-planar configurations for point of care tests, the conjugate containing one of the binding partners of the analyte in question is preferably delivered from a different plane. The analyte-containing sample is collected directly from the source and preferably undergoes no prior treatment, elution, dilution, or concentration. The conjugate is made to come in contact with the sample by means of a sample compressor, also referred to herein as a compressor device. Compression aids in combining mobilized conjugate and sample. The sample compressor, which includes the conjugate in preferred embodiments, is preferably completely separate from the sample analysis device. The sample compressor is not part of the flow path on the test strip. As a result, the transfer of the conjugate and the sample to the sample analysis device, which is preferably a test strip, is initiated using pressure, not flow or capillary action. After the sample compressor is applied, if necessary there may be a time lapse before applying the running buffer. This time lapse between sample application and the initiation of the testing by the flow can be up to 24 hours or many days depending on the stability of the analyte. The non-test strip components, including, depending upon the embodiment, any combination of the sample compressor, the sample collector, and one or more external binding partners, preferably remain associated with the test strip until flow is initiated.

A lateral flow device of the present invention may be an immunoassay using antibodies or a non-immunoassay using no antibodies but instead using other binding partners, including, but not limited to, nucleic acids, nanoparticles, ligands, and receptors.

Before further description of the present invention, and in order that the invention may be more readily understood, certain terms have been defined here as they relate to the present invention:

The term "compression" as used herein refers to the application of the sample and any components on a pad of a sample compressor to the test strip. The pad, the collection portion of the sample collector, and the sample application zone are all preferably compressible such that compression of the three occurs during application of the sample to the test strip.

The term "pressure" as used herein refers to physical pressure, and more specifically, physical pressure applied by a sample compressor to a sample on a sample collector and, in turn, to a sample application zone of a test strip. As used herein, pressure, which may be supplied by a mechanical bias or a user of the lateral flow device, brings the pad of the sample compressor, the collection portion of the sample collector, and the sample application zone of the test strip into physical contact to transfer the sample and any components on the pad of the sample compressor to the test strip. This transfer preferably does not occur by vertical flow.

The terms "vertical" and "vertically" as used herein refer to the direction parallel to the thickness or depth, as opposed to the length and width dimensions of the elements utilized in the device, such as the pads or mediums.

The terms "lateral" and "laterally" as used herein refer to the direction parallel to the length, as opposed to the width and depth dimensions of the elements utilized in the device, such as the pads and mediums.

In some embodiments, many of the elements of the test strip are substantially planar and have a lateral dimension that is greater than the vertical dimension. The magnitudes of these dimensions relative to each other, however, may be changed within the spirit of the invention. Generally, the terms "vertical", "vertically", "lateral", and "laterally" also refer to the juxtaposition or orientation of the elements of the device. For vertically juxtaposed elements, a line normal to and intersecting the planar surface of one such element is also substantially normal to and intersects the planar surface of the other vertically juxtaposed elements.

The term "flow path" as used herein refers to the path of capillary flow in a flow device during use of the device. The flow path in a conventional lateral flow device is laterally along the length of the device. In preferred embodiments of the present invention, the flow path is only lateral, because the sample is vertically transferred by compression using pressure rather than by flow. In contrast, vertical flow is used to transfer the sample to the test strip in the above-discussed prior art.

The term "label" as used herein refers to any atom, atoms, molecule, or molecules, such as a fluorescent tag, used to provide a detectable and preferably quantifiable signal. Methods of detection of the label include, but are not limited to, visible detection, fluorescence, chemiluminescence, radioactivity, colorimetry, gravimetry, X-ray diffraction, X-ray absorption, magnetism, and enzymatic activity. Visible spectrum test zones may be interpreted by a spectrometer to yield quantified test results.

The term "in situ lysis" as used herein refers to techniques for incorporating lysis agents into a point-of-care testing device, such as a chromatography test strip or other lateral flow immunoassay device, so that the lysis operation is not conducted as a separate step.

The term "zone" as used herein refers to any portion of the test strip. The boundaries of a zone are preferably planes perpendicular to the lateral direction. The term "zone" also encompasses the term "line", which refers to a zone having a length in the lateral direction significantly smaller than its width.

Embodiments of the present invention include assays where the analyte (target) to be detected does not bind directly to an immobilized binding partner in the test zone of a test strip. Instead, the analyte preferably interacts with one or more analyte binding partners in other zones (or in the buffer, in some embodiments) on the strip. At least one of the analyte binding partners includes a first tag that forms a complex with a second immobilized tag in the test zone.

In preferred embodiments, a control zone binding partner is included on the sample compressor. With this design, if the conjugate zone on the sample compressor is not adequately compressed and made to contact the test strip, no control zone will develop even with a proper flow of the running buffer. Thus, the appearance of the control zone with both the negative and positive test samples indicates a true procedural control in the test.

In some embodiments of the present invention, when lateral flow begins, the test strip is no longer in compressive contact with the sample compressor and sample collector. In other embodiments of the present invention, however, the vertical stack is maintained during lateral flow to maximize transfer from the sample compressor and sample collector to the test strip. In yet other embodiments, the sample collector is removed from the vertical stack after application of the sample to the test strip, but the sample compressor is then maintained in contact with the test strip during lateral flow to maximize transfer from the sample compressor to the test strip.

The invention provides a sensitive and rapid method for the detection of analytes, e.g. pathogens, enzymes, immunologic mediators, nucleic acids, proteins, glycoproteins, lipopolysaccharides, protein adducts, tumor and cardiac markers, and/or low-molecular weight compounds, including, but not limited to, haptens. The methods and devices are suitable for diagnosis in human beings and animals, e.g. pets or livestock animals. The detection may include direct detection of the analyte and/or the detection of antibodies against the analyte, which are present in the fluid sample to be tested. Preferably, the method includes a parallel determination of a plurality of analytes. The pathogens are preferably selected from viruses or microorganisms, such as bacteria, fungi (e.g. yeast or molds) or parasites (e.g. amoebae or nematodes). The immune mediators are part of the inflammatory cascade and include, but are not limited to, antibodies, growth factors, complement, cytokines, lymphokines, chemokines, interferons and interferon derivatives, C-reactive protein, calcitonin, amyloid, adhesion molecules, antibodies, and chemo-attractant components. The low-molecular weight compounds may include drug or chemical molecules or complexes and metabolites formed by drug or chemical molecules.

The detection may include a direct detection of the target, e.g. the pathogen, and/or the detection of antibodies against the target, e.g. the pathogen which are present in the fluid sample to be tested. Preferably, the method includes a parallel determination of a plurality of targets.

Alternatively, the analyte of interest may be a low-molecular weight compound. In a preferred embodiment, the analyte to be detected is a drug molecule such as heroin or methamphetamine. In other preferred embodiments, the low-molecular weight compound is a small molecule, such as a hapten.

The invention also includes the detection of a plurality of pathogens, allergens, immune mediators, nucleic acids, or low-molecular weight compounds on a single chromatographic carrier. The sample analysis device may allow the simultaneous detection of a plurality of low-molecular weight compounds, immune mediators, nucleic acids, proteins, or pathogens. Although the sample is preferably a fluid, partially or substantially solid dry matter or mass may be tested as a sample in devices and methods of the present invention. For example, the fluid may congeal or harden, such as in a healing wound, be collected with the sample collector, and then transferred to the sample application zone. The sample may alternatively be a hardened part of a blister scraped from the blister which may be moistened by a body fluid near the blister site, such as when collecting a sample to be tested for a sexually-transmitted disease, or moistened by the flowing buffer on the test strip. The sample may be one or more exudates from wounds or blisters.

The body sample is preferably whole blood, serum, plasma, a mucous membrane fluid (of the oral, nasal, vaginal, anal, inner ear, and ocular cavities), cerebrospinal fluid (CSF), tear fluid, penile fluid, a secretion or exudate from a gland, or a secretion or exudate from a lesion or blister, e.g. lesions or blisters on the skin. More preferably, the sample is selected from oral, nasal, ocular, genital, and rectal fluids and secretions or exudates from skin lesions or blisters.

In some embodiments, the amount of liquid associated with the sample is insufficient to transfer the sample and/or any conjugate or second binding partner on the pad of the sample compressor to the sample application zone under compression; instead, the running buffer provides the additional fluid required for transfer of the sample and/or conjugate and/or second binding partner to the sample application zone of the test strip. In other embodiments, the sample and/or any conjugate or second binding partner on the pad of the sample compressor is transferred to the sample application zone upon compression. In alternate embodiments, the running buffer may be applied through the compressor.

In preferred embodiments, the sample is a fluid that does not drip or flow after it is collected. Instead, the fluid is a congealed mass, such that, after the sample is collected on the sample collector, the sample can be held vertically or even upside down, and the sample remains on the sample collector. For example, when an eye sample is collected and not subject to pretreatment, the sample remains on the sample collector even if held vertically or upside down, primarily due to surface tension. This is because the sample is effectively trapped and contained on the sample collector material, for example a sample collector fleece. In preferred embodiments, Polyethylene terephthalate (PET) fibers, such as Dacron® fibers, or nylon fibers are used because the binding is not specific or permanent, so these fibers "release" the analyte when wet. The phenomenon is similar to gently mopping up a spill by a paper towel such that the moisture is held in the pores and by the surface tension. Other materials that could be used for the sample collector fleece include, but are not limited to, polyesters, cellulose, rayon, calcium alginate, microengineered mechanical structures containing microcapillaries and/or microchannels, or other fabrics or meshes. In embodiments where a sterile collector material is needed to collect a human body fluid, materials that can be sterilized and are approved for bio-compatibility are preferably used.

A significant advantage of the method is that test results are provided within the medical consultation period, e.g. in a few minutes. Preferably, the results are provided in a time period up to 20 minutes, more preferably up to 15 minutes. The test may also be run up to 24 to 48 hours after the sample has been taken from the patient. Also, as the test is noninvasive, it poses very little risk to the patient. Thus, the best available treatment can be applied on a timely basis for a specific pathogen. A further advantage over prior art methods is that only a few microliters of sample are required to perform an analysis. The sample is preferably about 0.1 microliter to about 100 microliters, more preferably about 0.2 microliter to about 20 microliters and most preferably about 0.5 microliter to about 15 microliters.

The invention may be performed by means of a simple test kit. Handling of the test kit does not necessitate additional laboratory equipment, further handling of reagents, or instrumentation. Another important advantage of the invention described herein is that the detection limit is typically 10 to 100 times lower than currently available diagnostic tests, because samples do not require dilution before they are transferred to the analysis device. Therefore, the methods of the present invention are more sensitive and accurate than methods of the prior art.

If both the conjugate, which includes a first binding partner for the analyte and a detectable label, and a second binding partner for the analyte are located on the sample compressor, the sample analysis device can be manufactured and used to test for any analyte. The user would just need to choose the specific compressor that contained the binding partners that targeted the analyte of interest.

In some of the embodiments of the invention, a body fluid sample is non-invasively collected with a collection device or swab member. The collection step preferably includes wiping or dabbing the swab member over a surface of the body containing body fluid to be tested. Preferably, the swab member is sterile. The swab member may be dry or pre-treated with a fluid before the collection step.

In preferred embodiments, there is no pretreatment of the swab member, and the sample is collected and transferred to the sample analysis device without any treatment of the collected sample. By collecting the sample with a collection device and not subjecting the sample to pretreatment steps such as extracting and/or diluting the sample, degradation of the sample is avoided. The analyte to be tested preferably remains intact or in its native form surrounded or mixed with the other naturally occurring substances in the sample.

In the prior art, when the sample is extracted and diluted in buffer, the sample is often no longer intact. This may change the "conformation" of the analyte due to its stability or lability. By collecting a sample directly using a collection device and not pretreating the sample, the native nature of the sample is preserved in the concentrated form. Since this results in a higher concentration of sample in less volume, it increases the sensitivity of the test. In addition, with no dilution of the sample, the time of appearance and the intensity of the test zone are directly proportional to the analyte concentration. Using a spectrometer, it is possible to get absolute numerical quantification. In addition, not having to pretreat the sample makes the test easier, faster, and less expensive. It also permits the test to be performed in a clinical setting by doctors, nurses, or lab technicians. In test strips used to detect conjunctivitis, the sensitivity of the tests is comparable to the sensitivity of ultra-sensitive polymerase chain reaction tests.

The prior art methods and devices required pre-treatment. Some of the reasons that it was believed that pretreatment was necessary included the mistaken belief that pretreatment would result in a more homogeneous sample. Another reason was that it was believed that concentrated samples needed to be buffered before conducting a binding assay. Others described the need to wash the sample, remove contaminating particles and substances that potentially could cause a non-specific binding reaction and therefore a false positive test result. There was also a generalized belief in the prior art that a larger homogeneous sample produced the most sensitive and specific assay test results.

On the contrary, by not pre-treating the sample, the user maintains inhomogeneous, highly concentrated samples. As described by the material principle of interfacial polarization, in inhomogeneous dielectric materials there are charge distributions occurring at the interfaces of the phases making up the inhomogeneous dielectric. In an "intact" (undiluted or undisturbed) in vivo infectious body fluid sample the charges or charge carriers are impeded by trapping at impurity centers or at the phase interfaces. The characteristic of this "intact" sample results in a two layer capacitor effect resulting in space-charge polarization. The characteristic of an "intact" inhomogeneous nature results in higher binding efficiency and therefore a more sensitive assay.

It was previously unknown what effects body fluids, including blood, tears, and purulent exudates, would have on different collector fleece materials. Specifically, it was unknown whether the analytes would be effectively released from the other cellular material and transferred from a sample collector to a sample analysis device.

In some embodiments, the sample size is preferably a few microliters. After transfer of the sample to the sample application zone (preferably without treating the sample), elution medium (also known as running buffer) is added. Prior art methods of running lateral flow immunoassays were unable to perform this washing step. For example, when collecting an eye sample to test for eye infections such as conjunctivitis, the sample size is preferably 3 to 15 microliters. In this example, 150 to 200 microliters of elution medium is then added to the test strip. As a comparison with different assay systems, this 40 to 50 fold washing exceeds the washing performed in machine dependent ELISA tests.

In one example of collecting a sample, using a gentle swirling motion, a sterile swab member may be applied to the body surface or mucous membrane of concern and allowed to capture any pathogens, low-molecular weight compounds, and/or immune mediators, peptides, glycoproteins, nucleic acids, and allergy-related components contained in the body fluid.

The swab member may be a part which is separate from the sample analysis device. The sample is then transferred by contacting the swab member with the sample analysis device and the sample compressor under conditions, where at least part of the sample is on the swab member. At least part of the conjugate in embodiments where the conjugate is located on the sample compressor and/or at least part of the second binding partner in embodiments where the second binding partner is located on the sample compressor are also transferred to the sample analysis device due to pressure. This is a similar phenomenon to squeezing the fluid out of a sponge. In this embodiment, the swab member preferably contacts both a sample application zone on the analysis device and the pad portion of the sample compressor (which preferably includes the conjugate and/or a second binding partner for the analyte). The sample and conjugate are then transferred to the sample application zone and then travel to the detection zone. In some embodiments, the swab member may be fixed in a contact position with the sample analysis device in which the sample collection zone of the swab member is in direct contact with the sample application zone of the analysis device. Thus, the swab member and/or the analysis device preferably includes fixing means for providing a fixed contact between both parts in a predetermined position. Alternatively, the swab member may be an integrated part of the sample analysis device and the transfer includes passing at least a part of the sample on the swab member, as well as the conjugate, to the sample application zone by exerting pressure using the sample compressor. In some embodiments, the sample compressor is also an integrated part of an integrated sample analysis device and is preferably connected to the device by a hinge. In other embodiments, the sample compressor is separate from the remainder of the device.

The transfer of the sample from the swab member to the sample application zone on the sample analysis device is preferably a direct transfer, i.e. the transfer takes place without pretreatment of the sample on the swab member. In embodiments without pretreatment of the sample or the swab member, microfiltration occurs in the region where the swab member fleece directly contacts the fleece on the strip. The fibers of the fleece interlock to form a grating or physical interference. Thus, larger elements contained in the sample are held back and not eluted on the sample analysis device. As the conjugate and the sample move through the sample application zone, the smaller analytes are eluted. Also, when using samples from mucous membrane fluids, mechanical disruption of the mucous in mucous membrane bodily fluids purifies the sample and the analyte of interest.

In other embodiments, the transfer includes an elution of the sample from the swab member with an elution medium, e.g. a buffer or water. The elution medium may be added from an external source or may be provided, e.g. as a reservoir, within the analysis device. Further, the transfer is preferably a chromatographic and/or capillary transfer of fluid to the detection zone on the sample analysis device.

In some preferred embodiments, the swab member is placed between a lateral flow test strip and a pad portion of a sample compressor (which may include the conjugate that includes a first binding partner for the analyte and a detectable label, a second binding partner for the analyte that includes a tag, a control zone binding partner, or any combination of any of these). With this step, the collected specimen is transferred directly onto a test strip. The test strip preferably includes one or several capillary active fleeces or membranes.

In some preferred embodiments, the sample is added to a chromatographic test strip, and the conjugate is added as a separate step after the sample is added. In these embodiments, the conjugate and the sample are not added simultaneously. For example, a sample collector including the sample is placed on a sample application zone of a test strip. At least some of the sample is transferred to the test strip at this time. Then, the sample compressor containing the conjugate is added and the sample compressor compresses the sample collector. This facilitates further transfer of the sample, as well as transfer of the conjugate, onto the test strip. If analyte is present, a complex between the analyte in the sample and the conjugate may be formed as soon as the conjugate begins compressing the sample. With fluid samples, the complex starts forming due to the fluid nature of the sample itself. In preferred embodiments, the second binding partner for the analyte is also either on the sample compressor or in the sample application zone of the test strip. In these embodiments, the full sandwich between the first binding partner, the analyte and the second binding partner may be formed before buffer is even added. Addition of buffer further enhances complex formation and then transport of the components to the detection zone. Since the complex can form during compression, there may be a time lag between sampling and testing. The reaction between the analyte and the conjugate preferably begins before buffer is added to the test strip. The time lag between when the sample and the conjugate are added and when buffer is added can be up to 24 hours or even longer.

The detection process will be either started directly with sample transfer or may require an elution medium to be applied for sample analysis. In some embodiments, the elution medium is simple tap water. In other embodiments, the elution medium is an alkaline buffer solution. In the case of an immunochemical test strip where the detection zone is laterally downstream of the sample application zone, the chosen elution medium moves towards a detection zone and thereby passes the contact site within the collection device. The analyte and the conjugate are eluted by the elution medium and carried with it to the detection zone. In the detection zone, the analyte is determined by qualitative and/or quantitative methods, e.g. in an immunological binding reaction.

The test strip can be made of one single chromatographic material, or preferably several capillary active materials made of the same or different materials and fixed on a carrier backing. These materials are in close contact with each other so as to form a transport path along which a liquid driven by capillary forces flows from the start zone, passing the contact site of the swab and the detection zone, towards a waste zone at the other end of the strip.

Some preferred materials and membranes for the test strip include, but are not limited to, polyethylene terephthalate (PET) fibers, such as Dacron® fibers, nitrocellulose, polyester, nylon, cellulose acetate, hydrogel, polypropylene, glass fibers, and combinations of these materials and their backings. The characteristics of the fleeces and membranes depend upon the types of materials used for a particular region or zone of the test strip or collection device. As described herein, materials that allow reagents (including those in the reagent zone, the capturing zone, or any of the other zones described herein) to be mobile and travel with the elution medium include fleece materials or fibers, where the binding is not specific or permanent, so that the analyte and reagents may be released when they encounter the elution medium or with large sample volume. Some of these materials include, but are not limited to, polyethylene terephthalate (PET) fibers, such as Dacron® fibers, nylon fibers, polyester fibers, cellulose acetate fibers, polypropylene fibers, glass fibers, foam, sponges, and other fabrics and meshes. In contrast, materials that immobilize reagents in a particular zone (including, for example, the reagents immobilized on the test zone and control zone of the detection zone and the capturing reagents in the embodiments that include capturing reagents immobilized in a capturing zone downstream of the sample application zone) include, but are not limited to, nitrocellulose and nylon fibers chemically treated such that individual fibers in the nylon mesh bind permanently to reagents such as proteins. Some methods for manufacturing different portions of the strip include, but are not limited to, striping, spraying, soaking, and drying materials onto the strip.

While nitrocellulose is used for the detection zone in many of the embodiments of the present invention, in other embodiments, neutral membranes, such as nylon or polyester may be used. In these embodiments, proteins, such as neutravidin, antibodies and antigens, nanoparticles, or nucleic acids are not immobilized directly. They are instead conjugated to microspheres which are "deposited" into the membrane and are held in the crevices.

Some preferred materials for the pad portion of the sample compressor include, but are not limited to, polyethylene terephthalate (PET) fibers, such as Dacron® fibers, nylon fibers, polyester fibers, cellulose acetate fibers, polypropylene fibers, glass fibers, fleece, foam, sponges, and other fabrics and meshes.

The test strip materials preferably filter and/or retain particulate matter, as well as cell debris, the precipitates, etc., in the membranes. In addition, since the volume of the sample is preferably so small, the sample stays put in the materials and the elution buffer flowing directly underneath the sample contacts and transports the sample such that the sample may be extracted, lysed, and/or filtered before it reaches the test zone of the detection zone.

Furthermore, devices and test kits of the present invention preferably perform the methods described herein.

In preferred embodiments, the conjugate is located on a sample compressor, separate from the sample analysis device. The conjugate preferably includes a first binding partner for the analyte, as well as being labeled with a detectable label. The label is preferably detectable visibly and/or by fluorescence, but any form of detection known in the art may be used, depending upon the label chosen.

In some embodiments, the detectable label for the conjugate can be colloidal gold, colored latex beads, fluorescent nanoparticles, chemiluminiscent nanoparticles, paramagnetic nanoparticles, or phosphorescent nanoparticles.

Qualitative interpretation is performed visually by observing the test zone intensity and hue. In an example where a visual red dye is used as the label, when the concentration of the analyte is equal or slightly above the lower limit of detection, the test zone can be seen faintly and the hue is pink. As the concentration of the analyte is increased, the test zone intensity correspondingly increases and the hue shifts from pink to bright red. A quantitative interpretation is developed using a spectrometer operating in the visible spectrum. Either an absorption measurement or a reflectance measurement may be used in the visible spectrum to develop the quantification of the test zone. First a set of characterized concentrations of the analyte are developed. Each of the concentrations is applied to the sample application zone and the test is run. The spectrometer is used to measure either the absorption or the reflectance of the test zone. A standard curve is calculated from the measured values of the spectrometer. The standard curve is normally linear. In other embodiments, if fluorescent tags are used, a similar set of known concentrations of the analyte may be developed. An unknown concentration of the analyte tested and quantified by the spectrometer yields a value that, when plotted on the standard curve, can be correlated to a concentration of analyte.

The visual label may be any label visible to the naked eye, including, but not limited to, colored particles such as colloidal gold, dyed latex beads, selenium, or carbon. In some embodiments, the visual tags are also coated with fluorescing elements. In some embodiments, the fluorescing element is a fluorescing dye. Alternatively, a mixture of preferably colorless fluorescing latex bead conjugates is mixed with colloidal gold (a visible spectrum) conjugates, or conjugates producing a visible read test zone, in lateral flow immunoassays to enhance sensitivity of the assay and to aid in visually reading true positives and true negatives. In embodiments where nanoparticles are used, the nanoparticles that may be used include, but are not limited to, selenium, carbon, and colloidal gold.

In some embodiments, a second binding partner for the analyte is also located on the sample compressor. The second binding partner includes a tag but not a detectable label. The second binding partner may alternatively be located in the sample application zone of the test strip, upstream of the sample application zone, or in any location on the test strip between the sample application zone and the detection zone. In embodiments where there is a second binding partner for the analyte either upstream of the detection zone or on the sample compressor, the detection zone includes an immobile tag that binds to the tag portion of the second binding partner.

In one preferred embodiment, the second binding partner is tagged with biotin. In embodiments where the tag on the second binding partner is biotin, the immobilized tag in the detection zone is preferably avidin, neutravidin, or streptavidin. In other embodiments, the second binding partner is tagged with avidin, neutravidin, or streptavidin. In these embodiments, the immobilized tag in the detection zone is preferably biotin. Alternatively, the tag on the second binding partner may be a lectin and the immobilized tag may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used.

In a preferred embodiment, the specific binding partners for the analytes in the conjugate zone on the sample compressor and/or in the sample application zone are monoclonal, polyclonal, or recombinant antibodies or fragments of antibodies capable of binding to a pathogen. In other embodiments, specific binding partners may also be antigens capable of binding to antibodies against a pathogen, an immune mediator, peptides, glycoproteins, or an allergen. Other types of binding partners are bioorganic macromolecules like aptamers or receptors, nanoparticles, or nucleic acids. The methods and devices of the present invention can be used for any binding assays, and can avoid the use of antibody/antigens or nucleic acids, for example, in ligand-receptor binding assays and enzyme-substrate binding assays.

In all of these embodiments, a full "sandwich" is preferably created between the first binding partner of the conjugate, the analyte, and the second binding partner, at the sample application zone when the analyte is present. Alternatively, the full "sandwich" may form between the sample application zone and the detection zone, if either of the first binding partner or the second binding partner is located downstream of the sample application zone. The full sandwich then travels to the detection zone, where the tag on the second binding partner binds to the immobilized tag in the detection zone. Note that the complex between the tag on the second binding partner and the immobilized tag in the detection zone occurs regardless of whether or not the analyte is present. However, the complex is only detectable when the analyte is present and the conjugate (which includes a detectable label) has bound to the analyte.

In other embodiments, instead of having a second binding partner for the analyte either on the sample compressor or on the test strip upstream of the detection zone, an immobilized second binding partner for the analyte is located in the detection zone. In these embodiments, half of the "sandwich" forms between the first binding partner of the conjugate and the analyte, which then travels to the test zone, where the half sandwich binds to the immobilized second binding partner, completing the full "sandwich".

The device also preferably includes a control zone, which indicates whether the test was run correctly. In preferred embodiments, a control zone binding partner, for example a mobile control zone binding partner with a visual label, is also located on the sample compressor. Placing the mobile control zone binding partner, which binds to an immobilized binding partner in the control zone, on the sample compressor will indicate whether or not transfer of the conjugate occurred from the sample compressor to the sample application zone of the sample analysis device. This is a very useful control, since it is essential that the conjugate be transferred in order to detect the presence of the analyte.

The sample may be taken by a standard swab member as currently used in the physician's office or emergency rooms. This swab member is subsequently pressed into the sample application zone of the chromatographic test strip using the sample compressor.

In some preferred embodiments, instead of lysing cells "outside" of a point-of-care testing device, the present invention utilizes "in situ lysis". In these embodiments, the methods and devices of the present invention incorporate a lysis zone including at least one lysis agent as part of a lateral flow assay test strip, such as those discussed herein, or other lateral flow assay devices known in the art, in order to lyse the sample material in situ. In addition, a capturing zone captures interfering substances to increase the accuracy of the assay.

Following sample loading, sample traveling with the transport liquid encounters the lysis agent. The lysis agent will have been pre-loaded onto the test strip and is eluted by the transport liquid. In some preferred embodiments, the lysis agent has been dried into the test strip. Alternatively, the lysis agent may be pre-dried by freeze drying or lyophilizing and then pre-loaded into the test strip. In other embodiments, the lysis agent may be absorbed, adsorbed, embedded, or trapped on the test strip. In a preferred embodiment, the lysis agent is localized on the sample application zone or upstream of the sample application zone, so that the sample is lysed when it is transferred to the sample analysis device. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in the sample, upon being exposed in suspension to the lysis agent, are themselves lysed in situ. The analyte is preferably then exposed to both the labeled conjugate and the second binding partner, to form the sandwich before reaching the detection zone. Alternatively, the lysis agent may be included in the running buffer.

Alternatively, the lysis agent may be introduced to the test strip during a sample compression step. In one embodiment, the lysis agent is located on the pad of the sample compressor. Alternatively, the lysis agent may be dried on the swab member of the sample collector if the swab member does not need to be sterile. Otherwise, the swab member may be sterilized after addition of the lysis agent using sterilization techniques which do not damage the lysing ability of the lysis agent.

The concentration of lysis agent pre-loaded onto a test strip is preferably between 0.001% and 5% weight/volume. The volume to be pre-loaded depends on where the lysis agent is pre-loaded. Appropriate ranges are 1 to 10 microliters when pre-loaded into the sample collector fleece (the sample application zone) or 5 to 50 microliters when pre-loaded into the absorbent pad or into other locations within the test strip. Ideally, the amount pre-loaded should be approximately 3 microliters pre-loaded into the sample collector fleece or approximately 10 microliters pre-loaded into the absorbent pad or into other locations within the test strip.

Selection of a specific lysing environment and agent will depend on the analyte and the assay. pH and ionic strength are key to the lysing environment. As to pH established by the lysis agent, a pH below 4.0 tends to precipitate materials, especially proteins. Higher pH, above approximately 10.0, tends to lyse materials such as proteins and cells walls. Therefore, a pH of approximately 10.0 or above is preferable for many applications. Alternatively, lower pH may be preferred for nucleic acid targets.

As to ionic strength established by the lysis agent, both high and low ionic strength may be used to lyse. For example, a lower ionic strength (hypotonic) tends to break up erythrocytes. Water by itself can lyse erythrocytes. Higher ionic strength environments may be used to rupture certain cell walls and membranes.

As to specific lysis agents, they may be grouped and selected based on their properties: salts, amphoteric and cationic agents, and ionic and non-ionic detergents. Ammonium chloride ($NH_4Cl$) lyses erythrocytes. Other salts, including, but not limited to, high concentrations of sodium chloride (NaCl) and potassium chloride (KCl), may rupture certain cell walls and membranes. Other lysis agents are amphoteric agents including, but not limited to, Lyso PC, CHAPS, and Zwittergent. Alternatively, cationic agents including, but not limited to, C16 TAB and benzalkonium chloride may be used as a lysis agent. Both ionic and non-ionic detergents are often used to break or lyse the cell wall or cell membrane components such as lipoproteins and glycoproteins. Common ionic detergents include, but are not limited to, SDS, EDTA, Cholate, and Deoxycholate. Ionic detergents are good solubilizing agents. Antibodies retain their activity in 0.1% SDS or less. Common non-ionic detergents include, but are not limited to, Octylglucoside, Digitonin, C12E8, Lubrol, Triton X-100, Noniodet P-40, Tween 20, and Tween 80. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

Surfactants generally act as wetting agents and lower the surface tension of a liquid. This then allows easier spreading by lowering the interfacial tension between liquids. So, surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. Finally, some undesirable non-specific binding may be prevented at a Tween 20 concentration of 5%. In all cases, the total amount of lysis agent pre-loaded onto all locations of an individual test strip must be sufficient to lyse barriers to immunodetection, permitting practical operation of the test strip.

The lysis agent itself should not interfere with any other assay detector or indicator agents and thus does not interfere with any other assay interactions and reactions to such an extent as to prevent practical operation of the assay. A lysis agent should have sufficient shelf life to allow manufacture, distribution, and storage before use of a test strip in point-of-care testing.

In a preferred embodiment of the present invention, the lateral flow device of the present invention includes a sample-transporting liquid, which can be a buffer, a sample compressor, and a chromatography test strip containing one or several fleece materials or membranes with capillary properties through which sample flows. In a device and method of the invention, it is unnecessary to lyse the cells in the sample prior to applying the sample to the test strip.

FIG. 1 shows a sample analysis device (test strip) 1 and a sample collector 2. The sample collector 2 may be any type of sample collector 2 known in the art, for example the sample collector 2 could be a swab member. The sample 20 may include the analyte 3, as well as interfering particles 5 (which may include interfering proteins or interfering genes) and other interfering particles or cell debris 4. The sample analysis device 1 includes a conjugate zone 8 upstream of the sample application zone 18 in this figure. Although the conjugate zone 8 is shown upstream of the sample application zone 18 in this figure, the conjugate zone 8 may alternatively overlap the sample application zone 18 or be downstream of the sample application zone 18 within the spirit of the present invention. The sample application zone 18 is also a microfiltration zone, which preferably filters out cell debris and interfering particles 4 that are in the sample 20.

The conjugate zone 8 preferably includes both a mobile conjugate 15, which includes a portion that binds to the analyte 3 and a detectable label, and a control zone binding partner 16 with a detectable label, which may be, for example, a control zone antibody with a visual label. In some embodiments, the mobile conjugate is a test antibody conjugate with a visual label. The control zone binding partner 16 binds with an immobilized binding partner for it in the control zone 11 and indicates whether the test has run correctly. If the analyte 3 is present in the sample 20, the analyte binds to the conjugate 15, and the conjugate 15-analyte 3 complex travel to the test zone 10 in the detection zone 12. The analyte 3 then binds to an immobilized binding partner 17 for the analyte 3, to form the full "sandwich" in a sandwich-type assay.

The transfer of the sample from the sample collector 2 to the sample application zone 18 on the sample analysis device is preferably a direct transfer, i.e. the transfer takes place without pretreatment of the sample on the sample collector 2. In embodiments without pretreatment of the sample or the sample collector 2, pressure 14 is applied and microfiltration occurs in the region where the sample collector fleece directly contacts the fleece on the sample analysis device 1. The fibers of the fleece interlock to form a grating or physical interference. Thus, larger elements contained in the sample, for example cell debris and interfering particles 4 are held back and not eluted.

The sample application device 1 preferably also includes a blocking zone 9 that includes one or more capturing reagents. This blocking zone captures interfering proteins and/or genes 5 that may be in the sample 20. Capture of an interfering substance 4, 5 by one or more capturing reagents occurs when the capturing reagent interacts in some manner with the interfering substance to keep the interfering substance from interfering with the detection of the analyte. While a blocking zone 9 is shown in FIG. 1, the capturing reagents may be located in a capturing zone 9 made of materials that allow the capturing reagents to be mobile, in the elution medium, mixed and dried with the reagents, incorporated into the sample application zone, incorporated into the sample collector fleece material, and/or immobilized on an immobilizing material (for example, nitrocellulose) either as a line or a zone. Any of these or any combination of these may be used in the embodiments of the present invention, depending on the test and sample matrix.

The sample analysis device 1 also optionally includes an absorbent pad 7 upstream of the conjugate zone 8 and the sample application zone 18. Buffer is added and travels in the direction of the arrow 6 to elute the test components, including the sample 20, the conjugate 15, and the control zone binding partner 16, to the detection zone 12. The sample analysis device 1 also preferably includes a waste pad 13 at the downstream end of the device 1. The sample analysis device 1 may also optionally include a backing 23.

Figure 2A:
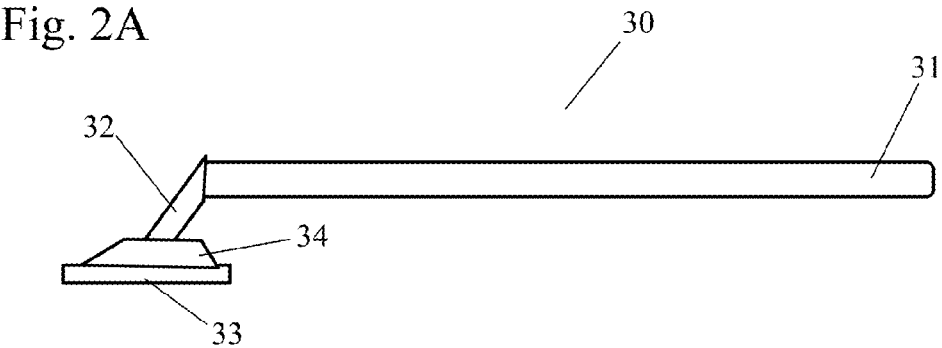
FIG. 2A shows a sample compressor in an embodiment of the present invention.
Figure 2B:
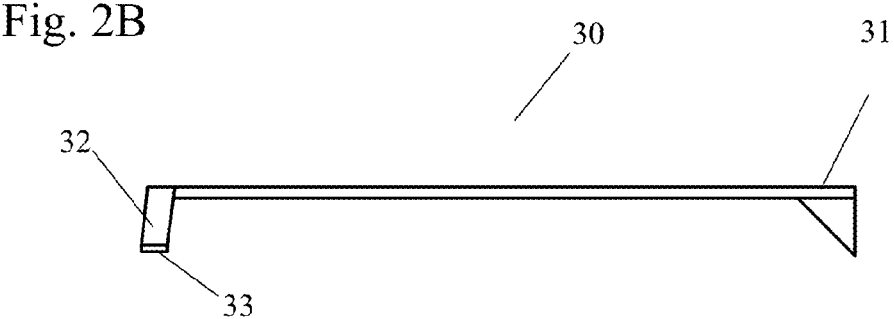
FIG. 2B shows another sample compressor in an embodiment of the present invention.

The devices and methods of the present invention include a sample compressor 30. Some schematic examples of sample compressors 30 that could be used are shown in FIGS. 2A and 2B. The sample compressors 30 preferably include a handle 31, an extended portion 32, and a pad portion 33. In some designs, the sample compressor includes additional sections, such as a ledge portion 34 that the pad portion 33 is placed upon. While specific examples are shown in FIGS. 2A and 2B, any sample compressor 30 that is able to exert pressure to transfer one or more components of the assay and the sample to the sample analysis device could be used in the embodiments of the present invention. In preferred embodiments, the conjugate 36 is pre-loaded and dried onto a pad 33 that forms the conjugate zone. In some preferred embodiments, a labeled control 61 that is able to complex with a binding partner at the control zone is also pre-loaded and dried onto the pad 33 of the sample compressor 30. In other preferred embodiments, the second binding partner 38 for the analyte is located on the pad 33. Any combination of the conjugate 36, the second binding partner 38, or the control zone binding partner 61 may be on the pad portion 33 of the sample compressor 30.

Figure 2C:
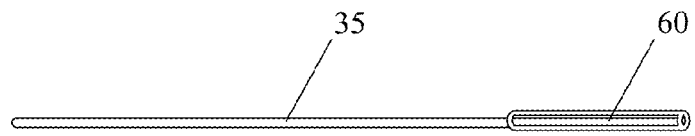
FIG. 2C shows a sample collector in an embodiment of the present invention.

FIG. 2C shows an example of a sample collector 35. In this example, the sample collector 35 is a swab member. The sample collector 35 preferably includes a sample collection portion 60, which is preferably made of fleece-type materials. In some embodiments, the sample collector 35 is sterile.

Figure 3B:
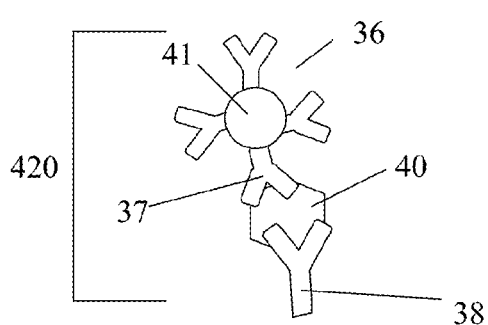
FIG. 3B shows a full sandwich including the analyte, the conjugate, and an immobilized binding partner in an embodiment of the present invention.
Figure 3A:
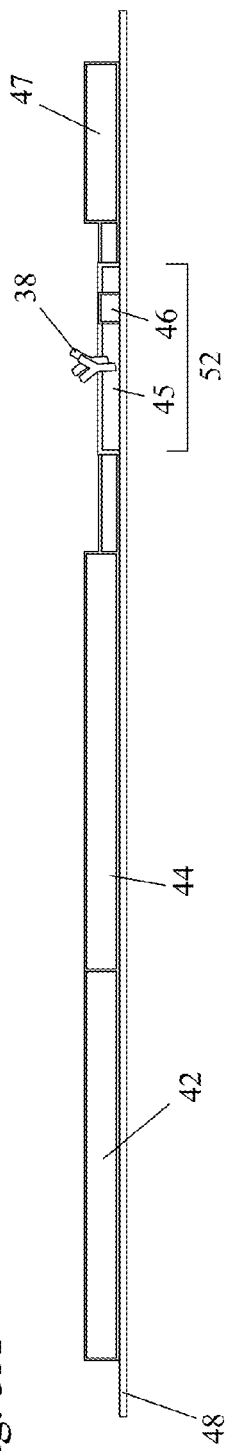
FIG. 3A shows a lateral flow test strip in an embodiment of the present invention.
Figure 3C:
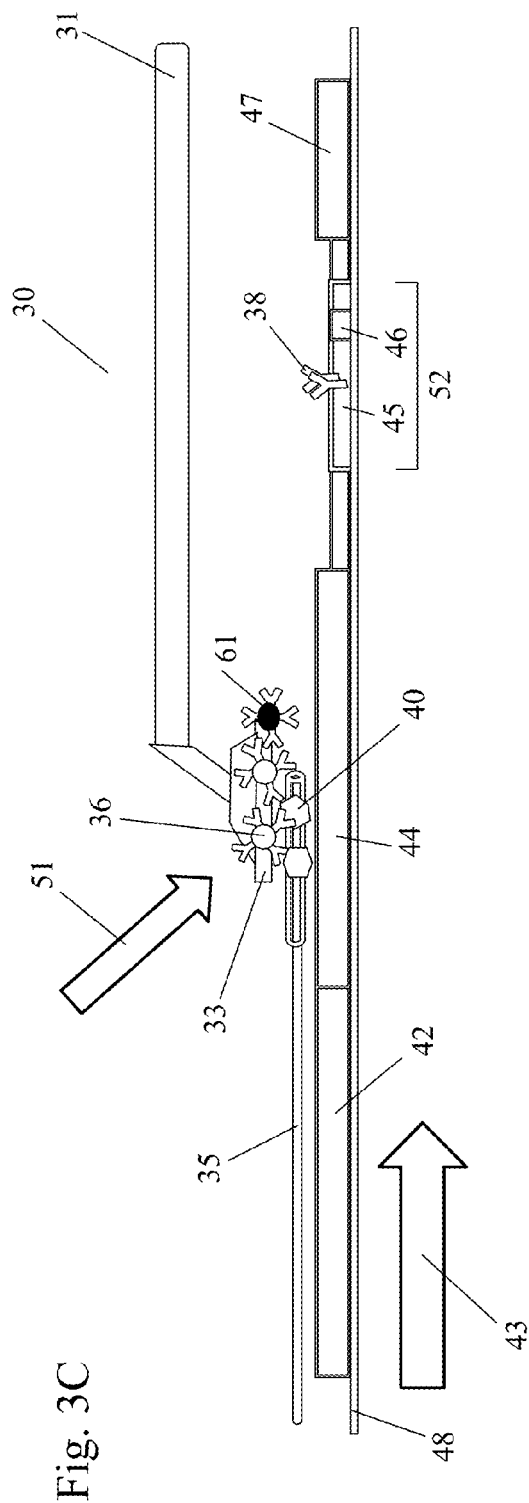
FIG. 3C shows a lateral flow device including the test strip of FIG. 3A, a sample collector, and a sample compressor in an embodiment of the present invention.

FIGS. 3A through 3C show one embodiment of a system with a sample compressor 30, a sample collector 35, and a sample analysis device (a test strip in the figure). The test strip preferably includes an absorbent pad 42, a sample application zone 44, a detection zone 52, and an optional waste pad 47. The test strip also preferably includes a carrier backing 48. The detection zone 52 preferably includes a test zone 45, which includes an immobilized binding partner 38 for the analyte 40, as well as a control zone 46. In this embodiment, the conjugate 36 is on the sample compressor 30. The first binding partner 37, which is part of the conjugate 36, from the sample compressor 30 binds the analyte 40 in the test sample to form a half sandwich, which is then transported to the second binding partner 38 which is immobilized in a test zone 45. The full sandwich 420 that forms between the portion 37 of the conjugate 36 that binds to the analyte 40, the analyte 40, and the second binding partner 38 is shown in FIG. 3B. In preferred embodiments, the pad 33 on the sample compressor 30 also includes a control zone binding partner 61 with a detectable label. The control zone binding partner 61 complexes with its binding partner in the control zone 46. Including the control zone binding partner 61 on the sample compressor 30, instead of on the test strip or in the buffer as known in the prior art, permits the user to be sure that the components on the sample compressor 30, which, in this embodiment include both the conjugate 36 and the control zone binding partner 61, have effectively transferred to the sample analysis device and thus ensures proper operation of the system.

In one example, both the first binding partner 37 and the second binding partner 38 are different antibodies to the analyte. The control zone binding partner 61 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 3A-3C of the present invention can be used for any binding assays, and can avoid the use of antibody/antigens or nucleic acids, for example, in ligand-receptor binding assays and enzyme-substrate binding assays.

In operation, the sample collector 35 is placed such that the sample is directly above the sample application zone 44. In some embodiments, placement of the sample collector 35 above the sample application zone 44 is not simultaneous with placement of the sample compressor 30. In other words, in these embodiments, some of the sample is transferred to the sample application zone 44 before the sample compressor 30 is added to the vertical stack.

The sample compressor 30 exerts pressure 51 on the sample collector 35, using pressure to transfer the sample, including the analyte 40 (if present), and the conjugate 36 onto the sample application zone 44. If there is also a control zone binding partner 61 on the sample compressor 30, the control zone binding partner 61 is also transferred. Note that the transfer is due to pressure, not due to flow or capillary action. Then, buffer 43 is added to permit flow of the conjugate 36-analyte 40 complex (if present) to the detection zone 52. An immobilized binding partner 38 in the test zone 45 then binds the analyte, forming the complete sandwich. Since the conjugate 36 includes a label 41, the complex that forms is detectable and indicates a positive result. Proper operation of the test also results in a detectable positive result in the control zone 46 due to the interaction between the control zone binding partner 61 and its immobilized partner in the control zone 46.

Although it is not shown, there may also optionally be a lysis zone, which preferably overlaps or is upstream of the sample application zone 44. In other embodiments, there may be a blocking zone that includes capturing reagents, similar to the zone discussed with respect to FIG. 1.

In other embodiments, the conjugate zone can contain both the binding partners for the analyte in the sample to form a "full sandwich". One of the binding partners preferably has a suitable marker such as biotin, avidin, lectin, a glycosyl moiety, a specific ligand, or a specific receptor. The other can be conjugated to the appropriate nanoparticles as mentioned below. The full sandwich is then captured at the test zone where the binding partner of the suitable marker, including, but not limited to, avidin for biotin, biotin for avidin, glycosyl moiety for lectin, lectin for the glycosyl moiety, a receptor for the ligand, or a ligand for the receptor, is immobilized.

Figure 20A:
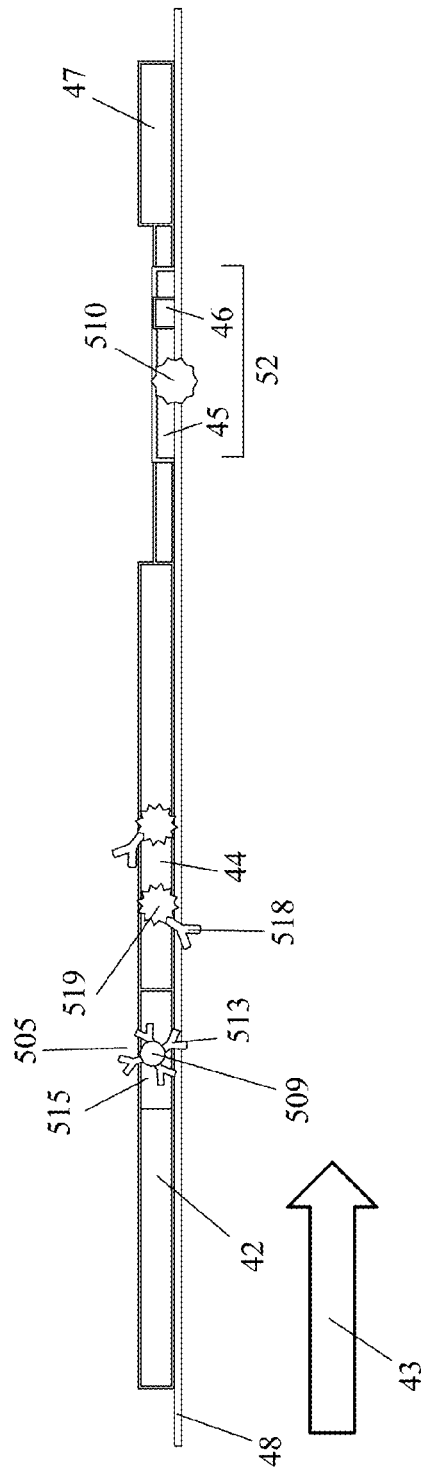
FIG. 20A shows a lateral flow test strip in an embodiment of the present invention.
Figure 20B:
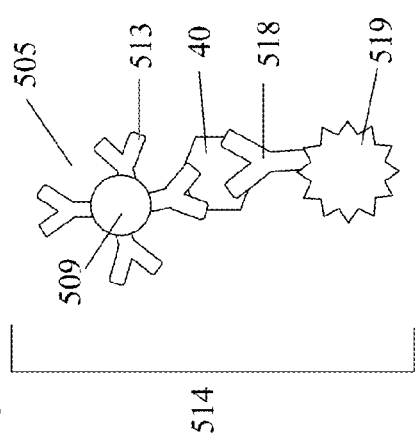
FIG. 20B shows a "full" sandwich, which preferably forms before reaching the test line, between the analyte, the labeled conjugate, and a second tagged mobile binding partner.

FIG. 20A shows an example of a test strip in an embodiment of the present invention. The test strip preferably includes an absorbent pad 42, a sample application zone 44, a detection zone 52, and an optional waste pad 47. The test strip also preferably includes a carrier backing 48. In this embodiment, the entire sandwich (first binding partner 513-analyte-40-second binding partner-518) forms in the sample application zone 44. The "full sandwich" 514 is shown in FIG. 20B. The test zone 45 in this embodiment includes an immobilized tag 510 that binds to the tag 519 of the second binding partner 518. The immobilized tag 510 does not bind directly to the analyte 40; instead, it binds through an intermediary, the tag 519 on the second binding partner 518 for the analyte 40.

In this embodiment, a first binding partner 513, which is part of the labeled conjugate 505, binds the analyte 40 in the test sample to form half a sandwich. The second binding partner 518 also includes a tag 519. The second binding partner 518 in this embodiment is preferably pre-loaded and dried on the sample application zone 44 of the test strip, while the labeled conjugate 505 is preferably pre-loaded and dried onto a labeled conjugate zone 515 upstream of the sample application zone 44. Alternatively, the second binding partner 518 and/or the labeled conjugate zone 515 may be located anywhere on the test strip upstream of the detection zone 52 including, but not limited to, overlapping the sample application zone 44, upstream of the sample application zone 44, or between the sample application zone 44 and the detection zone 52. In one preferred embodiment, approximately 75-80% of the labeled 509 conjugate 505 is upstream of the sample application zone (with approximately 20-25% of the labeled conjugate 505 overlapping the sample application zone 44) and approximately 75-80% of the second binding partner 518 is located downstream of the sample application zone 44 (with approximately 20-25% of the second binding partner overlapping the sample application zone 44). Although not preferred, in other embodiments, either the labeled conjugate 505, the second binding partner 518, or both may be located in the buffer or pre-mixed with the sample before the sample is added to the test strip. In still other embodiments, any or all of the components could overlap the detection zone 52.

In some embodiments, both the first binding partner 513 and the second binding partner 518 are different antibodies to the analyte 40. In other embodiments, specific binding partners may also be antigens capable of binding to antibodies against the analyte. Other types of binding partners are bioorganic macromolecules like aptamers or receptors, nanoparticles or nucleic acids. The device shown in FIG. 20A can be used for any binding assays, and can avoid the use of antibody/antigens or nucleic acids, for example, in ligand-receptor binding assays and enzyme substrate binding assays.

In one preferred embodiment, the second binding partner 518 is tagged 519 with biotin. In embodiments where the tag 519 on the second binding partner 518 is biotin, the immobilized tag 510 in the detection zone 52 is preferably avidin, neutravidin, or streptavidin. In other embodiments, the second binding partner 518 is tagged 519 with avidin, neutravidin, or streptavidin. In these embodiments, the immobilized tag 510 in the detection zone 52 is preferably biotin. Alternatively, the tag 519 on the second binding partner 518 may be a lectin and the immobilized tag 510 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, a sample collector containing the sample is placed such that the sample is directly above the sample application zone 44. In preferred embodiments, the sample has not been subject to pretreatment prior to application to the test strip. Instead, the sample is still in its native form.

The sample is transferred to the sample application zone 44 of the test strip. A sandwich forms with the labeled conjugate 505 as one piece of bread and the second binding partner 518 as a second piece of bread, with the analyte 40 in between them, when the three components come into contact with each other during flow 43. The labeled conjugate 505-analyte 40 (if present)-second binding partner 518 complex (a complete sandwich) flow to the detection zone 52. An immobilized tag 510 in the test zone 45 then binds the tag 519. Since the labeled conjugate 505 includes a label 509, the complex that forms is detectable and indicates a positive result. Proper operation of the test also results in a detectable positive result in the control zone 46, preferably due to the interaction between a control line binding partner and its immobilized partner in the control zone 46.

Although it is not shown, there may also optionally be a lysis zone, which preferably overlaps the sample application zone 44 or is alternatively located in other portions of the test strip within the spirit of the present invention.

In some preferred embodiments using tags, the detection zone includes an antibody against the tag. The antibody may be a monoclonal, polyclonal or single domain antibody. For example, when the tag is biotin, an anti-biotin antibody is immobilized in the test zone instead of avidin, neutravidin, or streptavidin.

Figure 4B:
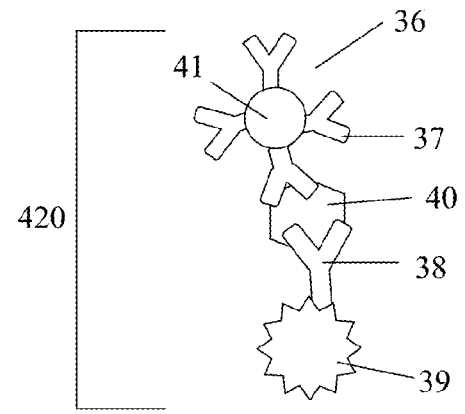
FIG. 4B shows a full sandwich including the analyte, the conjugate, and a tagged second binding partner in an embodiment of the present invention.
Figure 4A:
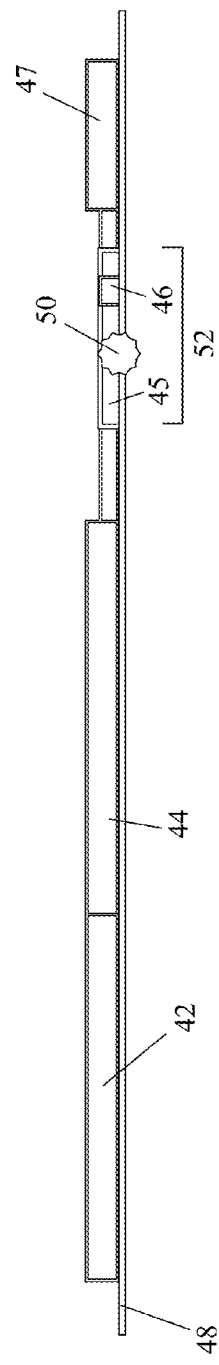
FIG. 4A shows another lateral flow test strip in an embodiment of the present invention.
Figure 4C:
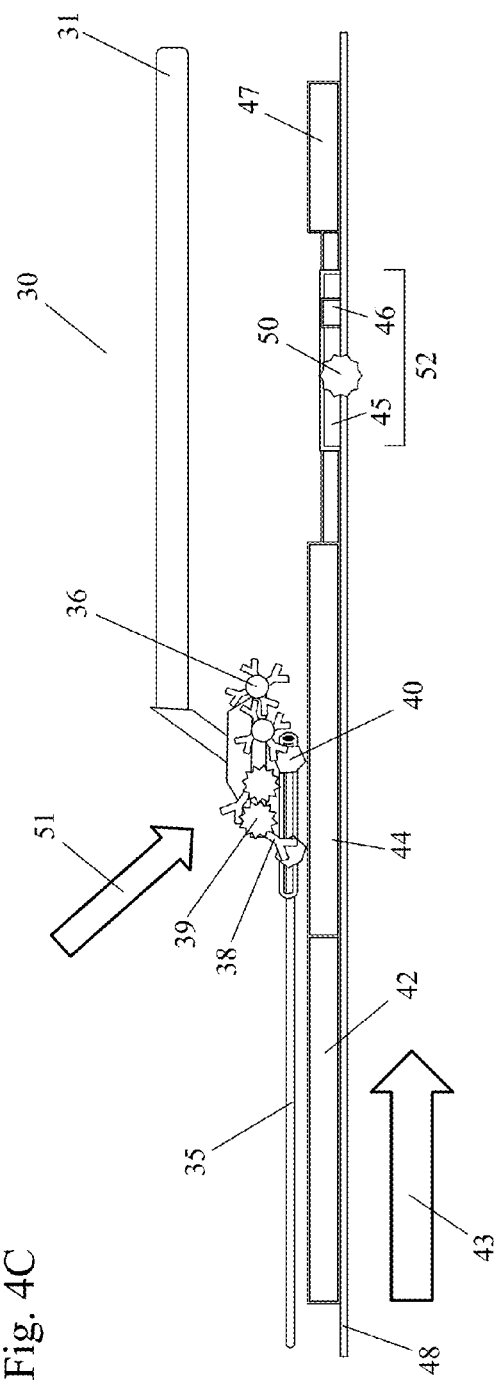
FIG. 4C shows a lateral flow device including the test strip of FIG. 4A, a sample collector, and a sample compressor in an embodiment of the present invention.

FIGS. 4A through 4C show an example of an embodiment of the system with a sample compressor 30, a sample collector 35, and a sample analysis device (a test strip in the figure). Similar to FIG. 3A-3C, the test strip preferably includes an absorbent pad 42, a sample application zone 44, a detection zone 52, and an optional waste pad 47. The test strip also preferably includes a carrier backing 48. In this embodiment, the entire sandwich (first binding partner 37-analyte-40-second binding partner-38) forms in the sample application zone 44 (preferably before the addition of buffer). In some embodiments, placement of the sample collector 35 above the sample application zone 44 is not simultaneous with placement of the sample compressor 30. In other words, in these embodiments, some of the sample is transferred to the sample application zone 44 before the sample compressor 30 is added to the vertical stack.

The test zone 45 in this embodiment includes an immobilized tag 50 that binds to the tag 39 of the second binding partner 38. In this embodiment, a first binding partner 37, which is part of the conjugate 36 and is preferably pre-loaded and dried on the pad 33 of the sample compressor 30, binds the analyte 40 in the test sample to form a half sandwich. The second binding partner 38 in this embodiment is also preferably pre-loaded and dried on the pad 33 of the sample compressor. The second binding partner 38 also includes a tag 39.

The full sandwich 420 that forms between the binding partner 37 of the conjugate 36, the analyte 40, and the second binding partner 38 in this embodiment (as well as the embodiments in FIGS. 5A-5B, 6A-6B, 7B, 7C, and 7D) is shown in FIG. 4B. In preferred embodiments, the pad 33 on the sample compressor 30 also includes a control zone binding partner 61 (shown in FIG. 3C) with a detectable label. The control zone binding partner 61 complexes with its binding partner in the control zone 46. Including the control zone binding partner 61 on the sample compressor 30, instead of on the test strip or in the buffer as known in the prior art, permits the user to be sure that the components on the sample compressor 30, which include both the conjugate 61 and the control zone binding partner 61, have effectively transferred to the sample analysis device and thus ensures proper operation of the system.

In one example, both the first binding partner 37 and the second binding partner 38 are different antibodies to the analyte. The control zone binding partner 61 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 4A-4C of the present invention can be used for any binding assays, and can avoid the use of antibody/antigens or nucleic acids, for example, in ligand-receptor binding assays and enzyme-substrate binding assays.

In one preferred embodiment, the second binding partner 38 is tagged with biotin 39. In embodiments where the tag 39 on the second binding partner 38 is biotin, the immobilized tag 50 in the detection zone is preferably avidin, neutravidin, or streptavidin. In other embodiments, the second binding partner 38 is tagged 39 with avidin, neutravidin, or streptavidin. In these embodiments, the immobilized tag 50 in the detection zone 52 is preferably biotin. Alternatively, the tag 39 on the second binding partner 38 may be a lectin and the immobilized tag 50 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, the sample collector 35 is placed such that the sample is directly above the sample application zone 44. The sample compressor 30 exerts pressure 51 on the sample collector 35. The pressure transfers the sample (including the analyte 40, if present), the conjugate 36, and the tagged second binding partner 38 onto the sample application zone 44. If there is also a control zone binding partner 61 on the sample compressor 30, the control zone binding partner 61 is also transferred. Note that the transfer is due to pressure, not due to flow or capillary action. Then, buffer 43 is added to permit flow of the conjugate 36-analyte 40 (if present)-second binding partner 38 complex (a complete sandwich) to the detection zone 52. An immobilized tag 50 in the test zone 45 then binds the tag 39. Since the conjugate 36 includes a label 41, the complex that forms is detectable and indicates a positive result. Proper operation of the test also results in a detectable positive result in the control zone 46 due to the interaction between the control zone binding partner 61 and its immobilized partner in the control zone 46.

Although it is not shown, there may also optionally be a lysis zone, which preferably overlaps the sample application zone 44. In other embodiments, there may be a blocking zone that includes capturing reagents, similar to the zone discussed with respect to FIG. 1.

In another embodiment, the two binding partners for the analyte are located in such a way to achieve a "vertical sandwich" where the sample binds with the conjugate being compressed from the second plane and can bind simultaneously or concurrently with the other binding partner located on the strip in the plane of the strip. Thus a sandwiching of the analyte in the sample is achieved by binding to the partner from the conjugate delivered from above the plane of the strip and binding to the second binding partner located on the plane of the strip below the sample delivering material.

FIGS. 5A and 5B show another example of an embodiment of the system with a sample compressor 30, a sample collector 35, and a sample analysis device (a test strip in the figure). Similar to FIG. 3A-3C, the test strip preferably includes an absorbent pad 42, a sample application zone 44, a detection zone 52, and an optional waste pad 47. The test strip also preferably includes a carrier backing 48. Similar to the embodiment shown in FIGS. 4A and 4C, in this embodiment, the entire sandwich (first binding partner 37-analyte 40-second binding partner 38) forms in the sample application zone 44. The test zone 45 in this embodiment includes an immobilized tag 50 that binds to the tag 39 of the second binding partner 38. In this embodiment, a first binding partner 37, which is part of the conjugate 36 and is preferably pre-loaded and dried on the pad 33 of the sample compressor 30, binds the analyte 40 in the test sample to form a half sandwich. The second binding partner 38 in this embodiment is preferably pre-loaded and dried on the sample application zone 44 of the test strip. The second binding partner 38 also includes a tag 39. Alternatively, the second binding partner 38 in this embodiment may be located anywhere on the test strip upstream of the detection zone including, but not limited to, overlapping the sample application zone, upstream of the sample application zone, and between the sample application zone and the detection zone.

In preferred embodiments, the pad 33 on the sample compressor 30 also includes a control zone binding partner 61 (shown in FIG. 3C) with a detectable label. The control zone binding partner 61 complexes with its binding partner in the control zone 46. Including the control zone binding partner 61 on the sample compressor 30, instead of on the test strip or in the buffer as known in the prior art, permits the user to be sure that the components on the sample compressor 30, which include both the conjugate 61 and the control zone binding partner 61, have effectively transferred to the sample analysis device and thus ensures proper operation of the system.

In one example, both the first binding partner 37 and the second binding partner 38 are different antibodies to the analyte. The control zone binding partner 61 is also preferably an antibody, and its binding partner at the control zone is an antigen (or vice versa). In other embodiments, specific binding partners may also be antigens capable of binding to antibodies against the analyte. Other types of binding partners are bioorganic macromolecules like aptamers or receptors, nanoparticles, or nucleic acids. The device shown in FIGS. 5A-5B of the present invention can be used for any binding assays, and can avoid the use of antibody/antigens or nucleic acids, for example, in ligand-receptor binding assays and enzyme-substrate binding assays.

In one preferred embodiment, the second binding partner 38 is tagged with biotin 39. In embodiments where the tag 39 on the second binding partner 38 is biotin, the immobilized tag 50 in the detection zone is preferably avidin, neutravidin, or streptavidin. In other embodiments, the second binding partner 38 is tagged 39 with avidin, neutravidin, or streptavidin. In these embodiments, the immobilized tag 50 in the detection zone 52 is preferably biotin. Alternatively, the tag 39 on the second binding partner 38 may be a lectin and the immobilized tag 50 may be a glycosyl moiety. For example, in some embodiments, the lectin is the Garden pea Lectin and the glycosyl moiety is an erythrocyte glycosyl unit. The tag on the second binding partner and the immobilized tag may be reversed within the spirit of the present invention. For example, the glycosyl moiety may be the tag on the second binding partner, with an immobilized lectin tag in the detection zone. In other embodiments, other receptors and ligands may be used for the tags.

In operation, the sample collector 35 is placed such that the sample is directly above the sample application zone 44. The sample compressor 30 exerts pressure 51 on the sample collector 35, using pressure to transfer the sample (including the analyte 40, if present) and the conjugate 36 onto the sample application zone 44. A "vertical" sandwich forms with the conjugate 36 as the top piece and the second binding partner 38 as the bottom piece, with the analyte 40 in between them. If there is also a control zone binding partner 61 on the sample compressor 30, the control zone binding partner 61 is also transferred. Note that the transfer is due to pressure, not due to flow or capillary action. Then, buffer 43 is added to permit flow of the conjugate 36-analyte 40 (if present)-second binding partner 38 complex (a complete sandwich) to the detection zone 52. An immobilized tag 50 in the test zone 45 then binds the tag 39. Since the conjugate 36 includes a label 41, the complex that forms is detectable and indicates a positive result. Proper operation of the test also results in a detectable positive result in the control zone 46 due to the interaction between the control zone binding partner 61 and its immobilized partner in the control zone 46.

Although it is not shown, there may also optionally be a lysis zone, which preferably overlaps or is located upstream of the sample application zone 44. In other embodiments, there may be a blocking zone that includes capturing reagents, similar to the zone discussed with respect to FIG. 1.

FIGS. 6A and 6B show another embodiment of the present invention, where the sample compressor 30 includes the second binding partner 38 for the analyte 40, coupled with a tag 39, and the test strip includes the conjugate 36, which includes both a first binding partner 37 for the analyte 40 and a detectable label 41, and the immobilized tag 50 that binds to the tag on the second binding partner in the test zone 45. This embodiment operates similarly to the embodiment described with respect to FIGS. 5A and 5B, except that the "vertical" sandwich forms with the second binding partner 38 as the top piece and the conjugate 36 as the bottom piece, with the analyte 40 in between them. Alternatively, the conjugate 36 in this embodiment may be located anywhere on the test strip upstream of the detection zone including, but not limited to, overlapping the sample application zone, upstream of the sample application zone, or between the sample application zone and the detection zone.

FIGS. 7A through 7D are similar to FIGS. 3C, 4C, 5B, and 6B, respectively, except that the detection zone 52 overlaps the sample application zone 44 in these figures. The detection zone in these embodiments is preferably made of nitrocellulose. Although no lateral flow is strictly required to run the assay in these embodiments, at least a nominal amount of flow is preferred such that the sandwich is able to bind in the test zone and any unbound conjugate is washed out of the test zone. In one embodiment, instead of a running buffer being applied to an end of the test strip, a washing fluid may be applied directly to the test zone, either from above or from the side, for example using a water bottle. In one embodiment, the sample compressor and the sample collector are substantially transparent so that the test zone can be read without removal of the vertical stack from the test strip. Note that, while both the test zone 45 and the control 46 are shown within the sample application zone in these figures, in other embodiments the test zone 45 could overlap the sample application zone 44 while the control zone 46 is downstream of the sample application zone 44. If the control zone was laterally downstream from the sample application zone 44, it would be necessary to add buffer to allow flow. In addition, it may be preferable to add a buffer, for example a buffer that includes silver, to enhance the signal from a positive result.

Figure 8A:
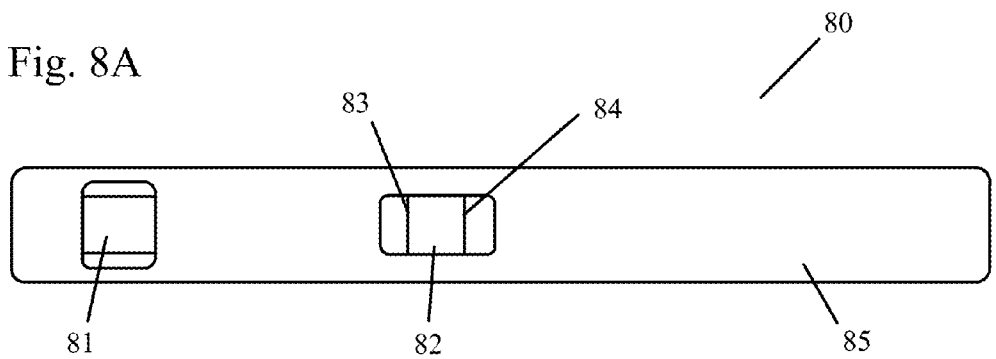
FIG. 8A shows a lateral flow device in an embodiment of the present invention.

A universal test strip 80, as shown in FIG. 8A, may be used when the sample compressor 30 includes both of the binding partners 37, 38 for the analyte 40. The sample compressor 30 and the sample collector 35 would be transferred to the universal test strip 80 at the sample window 81. Since the elements specific to the analyte 40 being tested are on the sample compressor 30, the test zone 83 in the viewing window 82 of the universal test strip 80 only needs to have a tag 50 that complexes with the tag 39 on the second binding partner 38 for the analyte 40. For example, when the second binding partner 38 for the analyte 40 is tagged 39 with biotin, the test zone 83 of the universal test strip 80 would include avidin 39, a binding partner for biotin. The universal test strip 80 also preferably includes a control zone 84 and a housing 85. For the embodiments of FIGS. 7A through 7D, the test zone is located in the sample window 81. In other embodiments, the suitable marker can be a nucleotide sequence that can hybridize with the suitable nucleic acid sequence immobilized at the test zone.

Although the sample compressor and the sample collector are shown as separate entities in FIGS. 1-8A, the pad 33 of the sample compressor and the sample collector portion 60 of the sample collector may be components of a single element within the spirit of the present invention. For example, the sample collector may be rotatably or flexibly or connected as part of a cartridge to the sample compressor, such that a sample can be collected from a patient with the sample collection portion without exposing the patient to the sample compressor pad and then the sample collection portion and sample compressor pad can be brought into contact for application to the sample application zone of the test strip by compression. The sample collector also may be rotatably or flexibly connected to the test cassette or may be inserted as a cartridge. In another embodiment, the sample may be forcibly injected directly onto the test strip prior to placing the compressor and/or conjugates into position. In yet another embodiment, the sample collector may contact the conjugates in an external cartridge that then snaps or inserts into a test cassette to bring the material in contact with the test strip.

Figure 8B:
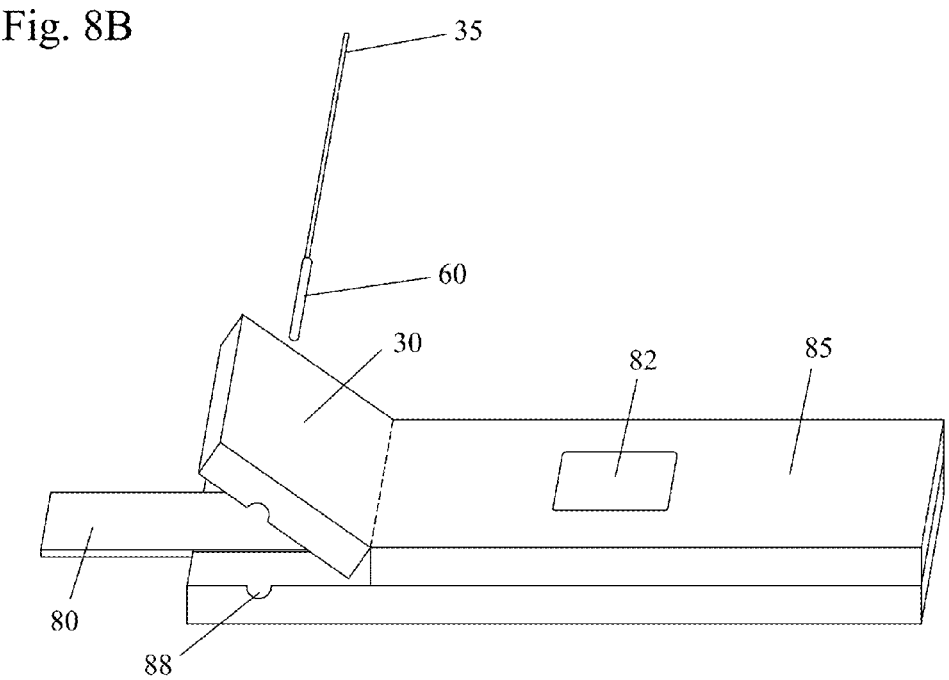
FIG. 8B shows another lateral flow device in an embodiment of the present invention.

In some embodiments, the sample compressor 30 is rotatably connected to the housing 85 as shown in FIG. 8B. While the hinge of the sample compressor 30 is shown such that the sample compressor 30 is rotated towards the downstream end of the strip when open, the housing could be designed such that the sample compressor 30 is hinged to either side or in other directions within the spirit of the present invention. The sample collection portion 60 of the sample collector 35 is preferably inserted from the side such that it lines up with an insertion hole 88 on the side of the housing 85. However, the sample collector 35 could be inserted in any direction depending upon the design of the housing. The sample compressor 30 preferably includes a pad (not visible in FIG. 8B), with one or more assay components, located on the surface of the sample compressor facing the sample application zone of the test strip 80. The sample compressor 30 is then closed such that a compression pressure is applied to the vertical stack of the pad of the sample compressor, the sample collection portion, and the sample application zone to transfer the sample and the one or more assay components to the sample application zone of the test strip. While there is an absorbent pad sticking out of the housing at the far upstream end of the device in FIG. 8B, the length of the absorbent pad may vary. In fact, as long as buffer can be added at the upstream end (for example, through an application window in the housing), it is not necessary to have the absorbent pad extend significantly outside the housing. In this embodiment, there is no possibility of losing the sample compressor, and there is no need to align the sample compressor with the sample application zone when forming the vertical stack. One advantage of these embodiments is that they allow for a time lapse between sample application and the actual initiation of flow to the test zone. In other words, the sandwich can be pre-made, and the flow initiated much later.

Alternatively, the pad 33 may be separate from the sample compressor within the spirit of the present invention. The pad may be on a binding partner applicator similar to the sample collector. In these embodiments, the binding partner applicator may be located between the sample collection portion and the sample application zone when the pressure is applied by the sample compressor to transfer the sample to the sample application zone.

Figure 9:
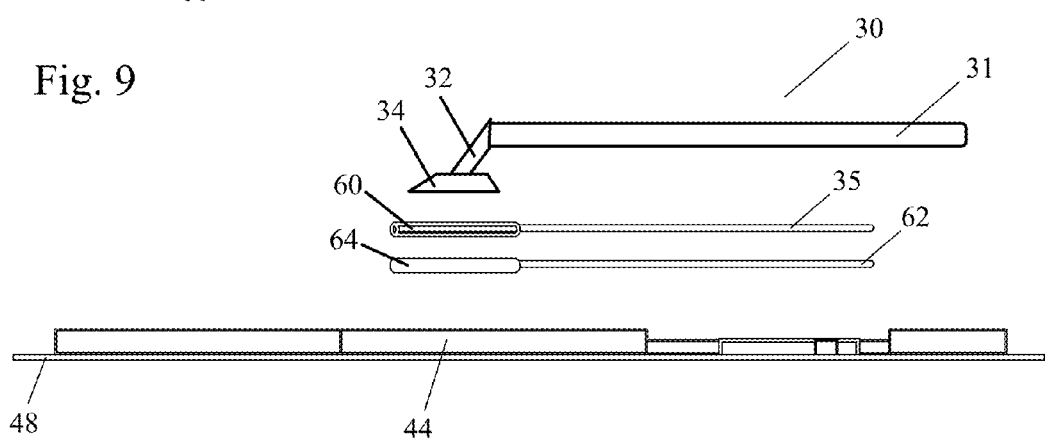
FIG. 9 shows a vertical stack in an embodiment of the present invention.

FIG. 9 shows a vertical stack including a sample compressor 30, a sample collector 35 with a sample collection portion 60, a binding partner applicator 62 with an applicator pad 64, and a sample application zone 44 of a test strip. While the binding partner applicator 62 includes a handle in FIG. 9, the binding partner applicator 62 could alternatively simply be a pad. The ledge portion 34 of the sample compressor 30 applies pressure to the sample collection portion 60 loaded with a sample and the applicator pad 64 loaded with at least one binding partner for an analyte to be tested for in the sample. The pressure preferably forces at least a portion of the sample from the sample collection portion 60 to wet the applicator pad 64, thereby mobilizing some of the binding partner such that at least some of the sample and some of the binding partner are transferred to the sample application zone 44. In some embodiments, this transfer occurs without dilution. In embodiments with small sample volumes or viscous or solid samples, however, an additional liquid may be used to facilitate transfer of the sample and the binding partner to the test strip. In some embodiments, as shown in FIG. 9, the sample compressor has no pad, although a pad may be used to aid in transfer, such as by supplying additional liquid or buffer, within the spirit of the present invention. In some embodiments, as shown in FIG. 9, the sample collection portion 60 is located between the sample compressor 30 and the applicator pad 64 in the vertical stack to aid in transfer of the binding partner to the test strip during compression. Alternatively, the applicator pad 64 may be placed between the sample compressor 30 and the sample collection portion 60 within the spirit of the present invention. In embodiments where the full sandwich forms prior to reaching the test zone, two binding partner applicators (a separate applicator for each binding partner of the analyte) may be used, with the sample collection portion, the first applicator pad, and the second applicator pad being placed in any order on the vertical stack within the spirit of the present invention. Alternatively, a single binding partner applicator could include both of the binding partners for the analyte. In other embodiments, the sample, the first binding partner, and the second binding partner may be applied sequentially to the test strip in any order using the sample compressor within the spirit of the present invention.

In a method of applying a sample to a test strip of a lateral flow device, at least one external binding partner is first placed on the sample application zone of the test strip. The external binding partner may be located on an external pad. In embodiments where there are two analyte binding partners that bind the analyte prior to reaching the test zone, either one or both of the analyte binding partners may be added. A sample collector that includes the sample is placed in a vertical stack between the external binding partner and a sample compressor. The sample compressor applies pressure to the sample collector to transfer the external binding partner and at least a portion of the sample to the sample application zone. Alternatively, the external binding partner could be added and compressed by the sample compressor, then removed, before the sample collector is stacked above the sample application zone, where the sample is compressed onto the test strip. In another alternative embodiment, at least one external binding partner is placed in the vertical stack between the sample compressor and sample collector. Alternatively, the sample collector is added and compressed, then removed, and then the external binding partner is added and compressed onto the test strip. In other embodiments, the sample collector is in a vertical stack between a first external binding partner and a second external binding partner, and the sample compressor applies pressure to the vertical stack. In these embodiments, neither the strip nor the sample compressor has a specific analyte binding partner. The sample, the analyte binding partner, and the mobile control binding partner may also be applied to the sample application zone in multiple steps in any combination within the spirit of the present invention.

Alternatively, in a lateral flow device of the present invention, the sample compressor may be a universal sample compressor with no components specific to the analyte of interest. In one embodiment, the sample compressor contains no components of the assay. In embodiments with a control, the pad of the sample compressor contains only the mobile control zone binding partner. In these embodiments, one or more binding partner applicators include at least one binding partner for the analyte and become part of the vertical stack with the sample compressor and the sample collector when the sample is transferred to the sample application zone. The sample, the analyte binding partner, and the mobile control binding partner may also be applied to the sample application zone in multiple steps in any combination within the spirit of the present invention.

In another embodiment of the present invention, the sample compressor 30 also serves as the sample collector, and the pad 33 of the sample compressor also serves as the sample collection portion. In this embodiment, the conjugate, the second binding partner, the control line binding partner, and/or any combination of the three, are preferably located on a back surface of the pad 33, where the pad is attached to the sample compressor arm. In embodiments where sample collection needs to be performed sterilely, the sample compressor 30 is then preferably sterilized by radiation prior to use as a sample collector. The sample is then collected using the front part of the pad so that the patient is not exposed to the conjugate or the second binding partner during sample acquisition. When the sample is applied to the sample application zone of the test strip, the pad is preferably compressed so that the sample mixes with the conjugate or the second binding partner and at least a portion of both is squeezed out onto the test strip.

In some embodiments, a lateral flow device of the present invention may also include a built-in, on-line, or in situ signal amplification system. The sample amplification system may be used in combination with a sample compressor or in a method or device without a sample compressor within the spirit of the present invention. In embodiments where colloidal gold is used as the detectable label for the conjugate, the signal of the colloidal gold in the conjugate bound to the test zone can be further amplified by silver enhancement. Suitable formulations of silver salts and the silver developers can be dried at the site of sample application or upstream to it or downstream to it. The silver salts and the developers can be dried together, upstream or downstream to each other, or can be separated by the sample application area. In other embodiments, stacking, where the system includes a conjugate with an additional antigen and a second conjugate, which is preferably a nanoparticle, with the specific binding partner of the antigen, is used to amplify the signal. The second conjugate also preferably includes a label. In the second conjugate, the binding partner may be conjugated to a particle that is the same size, smaller, or larger size than the particle in the first conjugate. In yet other embodiments, both the silver enhancement and the stacking enhancement may be used on the same test strip. The stacking conjugate and silver enhancement elements can be together or upstream or downstream to one another. A preferred feature of these embodiments is that both the "stacking" nanoparticles and/or silver enhancers do not come into contact with the conjugate initially but come into contact only while the conjugate is immobilized at the test zone. Thus, a better specificity is achieved.

In some embodiments where a "full sandwich" is formed between the analyte 40, the first analyte binding partner 37, and the second analyte binding partner 38 prior to the complex reaching the detection zone 52 (see, for example, FIGS. 4A-4C, 5A-5B, and 6A-6B), silver enhancement or other amplification signals may be placed upstream of the sample application zone 44 such that the silver salt and/or silver developer interacts with the full sandwich before the complex reaches the detection zone 52. In other embodiments with a full sandwich, the silver salt and/or silver developer are located downstream of the sample application zone 44 such that the full sandwich forms and travels to the silver salt/developer before reaching the detection zone 52.

Figure 10:
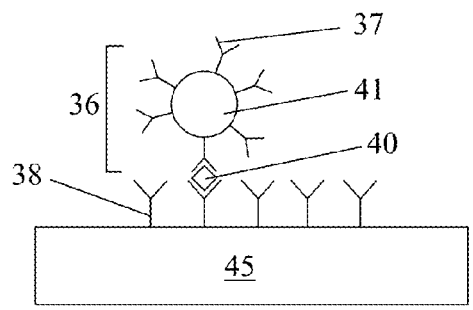
FIG. 10 shows a prior art gold conjugate sandwich in the test zone.

In the prior art as shown in FIG. 10, there is a one-to-one correspondence between analyte 40 and label 41 at the test zone 45, because each analyte binds to one immobilized binding partner 38 and one mobile binding partner 37 with one label 41 on the conjugate 36.

In a signal amplification system of the present invention, the amplification source may be located anywhere on the test strip, including at the sample application zone, or upstream or downstream of it. Alternatively, the source of amplification may be located in the buffer or on the sample compressor.

Figure 11:
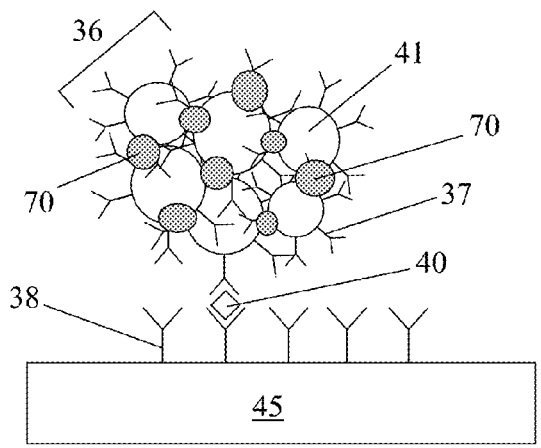
FIG. 11 shows a sandwich with signal enhancement in the test zone in an embodiment of the present invention.

In some embodiments as shown in FIG. 11, the amplification source 70 non-specifically deposits itself onto the conjugate such that multiple conjugates are associated with one analyte bound in the test zone. In this embodiment, the amplification source is preferably one or more silver salts, and a silver developer may be used to enhance the signal in assays using colloidal gold as the label portion 41 of the conjugate. The silver salts and silver developer may be located or introduced in any manner to enhance detection of the analyte. In embodiments where colloidal gold is used as the detectable label for the conjugate, the signal of the colloidal gold in the conjugate bound in the test zone can be amplified by silver enhancement. Suitable formulations of silver salts and the silver developers can be dried at the site of sample application or upstream to it or downstream to it. Silver salts and the developers can be dried together, upstream or downstream to each other, or separated by the sample application area. Alternatively, silver salts and/or developers can be included as part of the buffer.

In a preferred embodiment, the mixture of the silver salts and developers is dried in an area between the sample application zone and the test zone. In this embodiment, a full sandwich of the analyte between two binding partners (one being a conjugate on gold and the other suitably tagged with markers such as biotin) moves into the silver enhancing area and together travel to the test zone where they get captured. Although the silver enhancement may be applied to the half sandwich prior to capture, the silver enhancement is preferably applied after capture, because it may otherwise interfere with binding at the test zone. Silver salts and developers may be used in any of the embodiments described herein, including, but not limited to those shown in FIGS. 3A-3C, 4A-4C, 5A-5B, 6A-6B, and 7A-7D.

In yet another embodiment, the silver enhancing area is located directly underneath the sample application material. The compressor with both the binding partners as described above would form the full sandwich and become enhanced by silver salts and developers all in one place. This mega complex then can move into the test zone where it can be captured.

In yet another embodiment, the silver enhancement is achieved by incorporating the silver salts and the developers in the running buffer. In other embodiments, the silver salts and/or silver developer may be located on the sample compressor or the sample collector in situations where the sample collector need not be sterile. Otherwise, the sample collector may be sterilized after addition of the silver salts and/or silver developer using sterilization techniques, such as, for example, radiation, which do not damage the silver salts and/or silver developer.

In yet another embodiment, the silver salt are dried at the site, upstream, or downstream to the sample application area and the silver developer can be added to the viewing window as a separate step.

In a preferred embodiment involving the silver enhancement, since silver is light-sensitive, the test is run upside down (with the cassette turned over in embodiments where a cassette is used) or otherwise shielded from ambient light prior to the completion of the test.

In another embodiment, the silver enhancement is achieved as a separate step where the silver salt and the developer are added together or separately to the viewing window area 82 where the test zone 83 is located. If there is no viewing window area 82, the silver salt and the developer are preferably added to the test zone 83 of the strip. In some of these embodiments, the silver enhancement is added to the test strip while it is still wet or dried after the use. In some of these embodiments, the strip is removed from any housing and a portion of the strip containing the test zone 83 is cut and treated with silver enhancement together or separately.

In one preferred embodiment, after the test is run, the strip is allowed to dry in air. Moderate drying of the strip is accomplished in approximately 20 to 30 minutes, but is dependent upon environmental conditions. After the strip has dried, a drop or two of the silver salt and the developers are added to the viewing window area 82 where the test zone 83 is located. If there is no viewing window area 82, the silver salt and the developer are preferably added to the test zone 83 of the strip. This enhances the sensitivity at least 5 fold. The silver salt and the developers may be added together or separately. The silver enhancement occurs almost instantaneously and the results are preferably read within two to three minutes after the additional of the silver enhancement. If the results are not read quickly, the strip may turn black and the background will interfere with the reading of the resulting grey/black test line. This background can be largely minimized if a washing solution is added to the viewing window 82/test zone 83. Sensitivity may be further enhanced with the use of a portable optical reader, for example a miniature spectrometer made by Ocean Optics, Inc. (Dunedin, Fla.). A portable reader is a hand-held miniature spectrometer, which quantifies the color intensity of the test line measuring the absorbance or the reflectance of the labeled complex which binds to the test line. The quantification of the test line can be determined by the use of a standard curve. In developing a standard curve, one creates several titrations of the analyte concentration and records the reader output at each titration. The reader increases the sensitivity of a test by 5 to 10 fold. In operation, the detection window to view the visible test line is placed directly on or in proximity to the spectrometer aperture so that a direct absorbance or reflectance measurement can be made.

In another preferred embodiment, the silver salt and/or developer solution includes a volatile liquid. The silver salt and developer could be made up together in a single solution or as separate solutions. Any liquid that evaporates at room temperature or vaporizes easily and does not interfere with the test could be used. The volatile solvent is chosen in such a way that it does not dissolve the membrane material (e.g. nitrocellulose) that makes up the test zone 83 where the second binding partner 17 (see FIG. 1), 38 (see FIGS. 3A-3C and 7A) or the immobilized tag 50 (see FIGS. 4A-4C, 5A-5B, 6A-6B and 7B-7D) are located. Some examples of a volatile liquid that could be used include, but are not limited to, methanol, isopropyl alcohol, low concentrations of benzene, and low concentrations of acetone. The silver enhancement has the silver salt and a developer which is preferably relatively organic in nature. The silver salt and developer solution are added to the viewing window area 82 where the test zone 83 is located at the end of the test (for example approximately 10 minutes after the sample was added to the strip), when the strip is still quite wet. If there is no viewing window area 82, the silver salt and the developer are preferably added to the test zone 83 of the strip. The volatile liquid "dries" the area where the liquid is added (the test zone 83). In this embodiment, it is not necessary to wait for the entire strip to be moderately dry. This embodiment creates "in-situ" drying of only the area of interest (the test zone 83).

Figure 12:
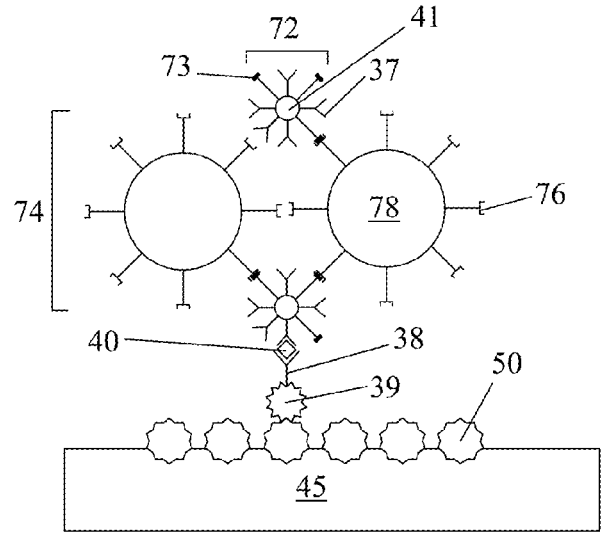
FIG. 12 shows a sandwich with stacking in the test zone in an embodiment of the present invention.

In some embodiments as shown in FIG. 12, the amplification is due to a "stacking" phenomenon where a second conjugate 74 "stacks" on at least a portion of the complex formed during the assay. In these embodiments, the first conjugate 72 includes an additional portion 73 to which a binding partner 76 of the portion 73 specifically binds, and the second conjugate 74 preferably also includes a label 78.

For example, when the second binding partner 38 includes an avidin tag 39, the full sandwich is captured in the test zone by immobilized biotin 50, and subsequently or concurrently, the "stacking" conjugate accumulates or gets stacked onto the immobilized full sandwich at the test zone, giving rise to more stacked accumulation and better signal perception. In one embodiment, the first conjugate is gold conjugated to an antibody of the analyte and chicken IgY, and the second conjugate is a red latex bead conjugated to a rabbit anti-chicken antigen.

Preferably, "stacking" is only used in embodiments where the "full sandwich" is formed prior to reaching the test zone. For example, in FIGS. 4C, 5B, 6B, 7B, 7C, and 7D, a full sandwich is formed in the sample application zone. In a preferred embodiment, mouse antibody on labeled conjugate binds to the antigen to form a first complex. The first complex immediately binds to the mobilized biotin labeled polyclonal antibody to form a full sandwich as a second complex. The second complex is then captured at the test zone by avidin via the biotin label. Slower released anti-mouse label conjugate then binds and stacks on to the mouse antibody in the second complex in the test zone. The anti-mouse label conjugate is preferably located such that it reaches the test zone after the analyte complexes have formed. Some preferred locations for the anti-mouse label conjugate include in the sample application zone, upstream of the sample application zone, added to the buffer after a predetermined amount of time, applied to the test zone after the sandwich has been formed, or in the flow path but encapsulated to delay its release, for example, by 20 to 30 seconds. In this embodiment, the stacking increases the sensitivity of the assay 3-5 fold.

In embodiments of the present invention with gold conjugates, which may be used in all lateral flow assays, labeled and dried anti-chicken IgY, or another nonspecific immunogenic moiety, is incorporated on the test strip upstream from the sample application zone or alternatively in the buffer. When the sample is mammalian (e.g., human), the nonspecific immunogenic moiety is preferably from a non-mammalian organism such as, for example, a bird, a fish, or a plant, so that it does not interfere with analyte binding. The second conjugate, e.g. anti-chicken IgY, is then mobilized by the buffer. Delaying the mobilization of the second conjugate allows the full sandwich to flow and begin binding via tag-immobilized tag, e.g. biotin-avidin, capture at the test zone in the case of a mobile second binding partner. The full sandwich accumulates at the test zone followed by binding and stacking of the second conjugate, e.g. red latex beads, on top of the first conjugate, e.g. gold. This embodiment also increases the sensitivity of the assay 3-5 fold. In embodiments where the second binding partner for the analyte is immobilized at the test zone, the half sandwich preferably travels to the test zone followed by binding and stacking.

FIG. 11 shows non-specific amplification and FIG. 12 shows specific amplification. In other embodiments, combinations of both specific amplification and non-specific amplification could be used, to further amplify the signal. As an example, the first amplification is due to a "stacking" phenomenon as shown and discussed above with respect to FIG. 12 where a second conjugate 74 "stacks" on at least a portion of the complex formed during the assay. Further amplification is provided when an amplification source 70 non-specifically deposits itself onto the conjugate such that multiple conjugates are associated with one analyte bound in the test zone, as shown and discussed above with respect to FIG. 11. Other combinations of specific and non-specific amplification could alternatively be used.

In another embodiment of stacking and signal enhancement, enhancement is performed using an enzyme conjugated to the stacking moiety. In one example, the enzyme is horseradish peroxidase, and it is conjugated to a rabbit anti-mouse antibody. While horseradish peroxidase is often used to amplify a weak signal, other enzymes that enhance weak signals could alternatively be used including, but not limited to, alkaline phosphatase, catalase, urease, and glucose oxidase. Similarly, other antibodies that bind to the conjugate or an intermediary could alternatively be used. There are no nanoparticles or microspheres in this embodiment. Instead, this embodiment includes a "soluble" form of the conjugate. The location where this enzyme conjugate is dried can vary; it can be upstream, downstream, or overlapping the sample application zone. In embodiments with a sample compressor, the enzyme conjugate could alternatively be on the sample compressor. The enzyme conjugate is preferably dried on the test strip, but not immobilized. It can be located alone or in combination with other components that form the "sandwich" with the antibody (which is preferably biotinylated) and/or the gold-conjugated antibody.

Figure 14:
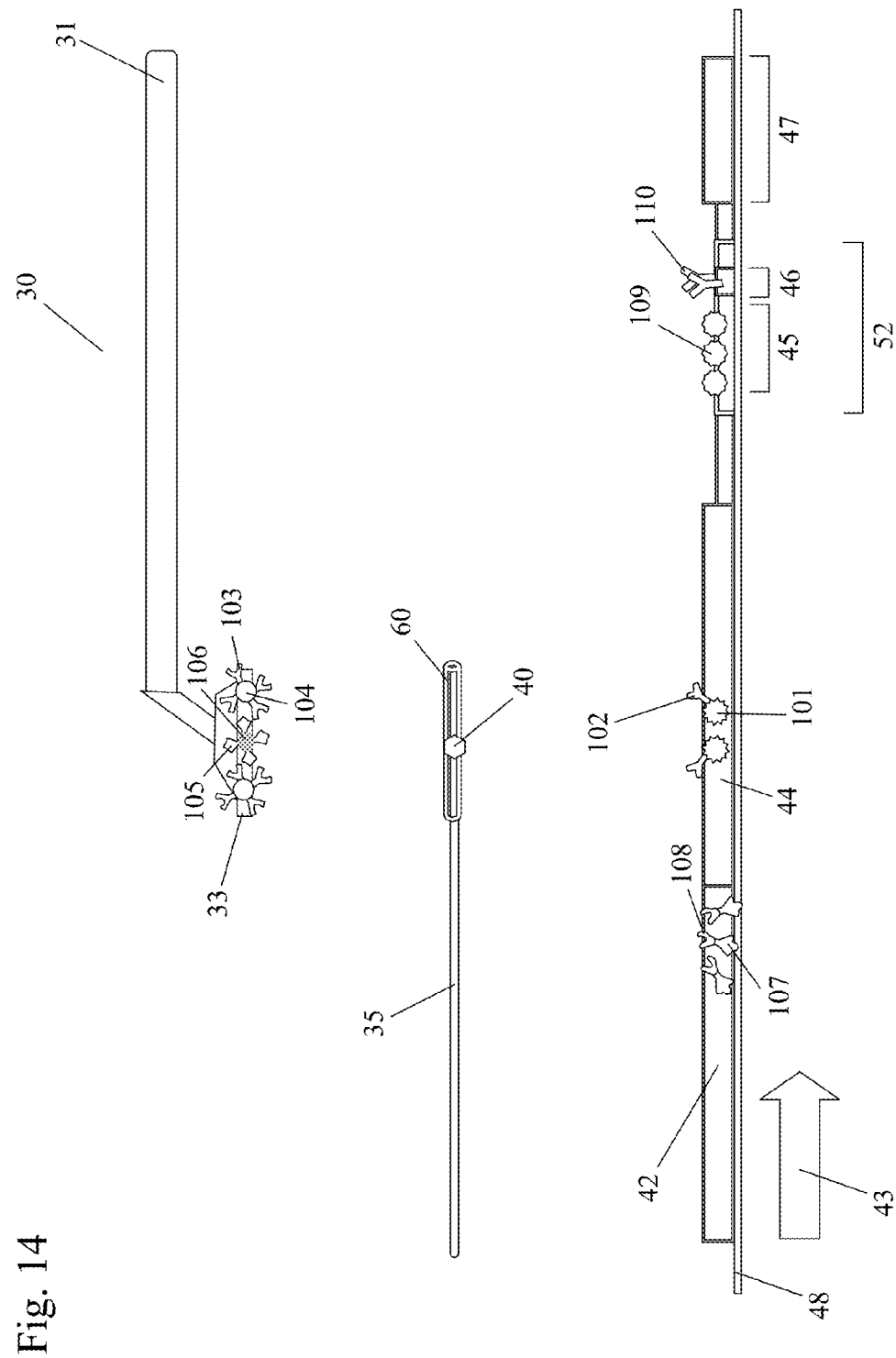
FIG. 14 shows a lateral flow device in another embodiment of the present invention.

FIG. 14 shows an embodiment of a detector with an enzyme conjugated to the stacking moiety. The control zone 46 includes an immobilized first control binding partner 110. The test zone 45 includes an immobilized first test zone binding partner 109 on the membrane. A first analyte binding partner 102 conjugated to a second test zone binding partner 101 is dried or otherwise incorporated (e.g., lyophilized) into the sample application zone 44. While not shown in this figure, the first analyte binding partner 102 could alternatively be located upstream or downstream of the sample application zone 44. A binding partner 107 for a second analyte binding partner 103 is conjugated to an enzyme 108, and is located upstream of the sample application zone 44. Alternatively, the binding partner 107 for the second analyte binding partner 103 could overlap the sample application zone 44 or be located downstream of the sample application zone 44. The pad 33 on the sample compressor 30 is preferably embedded with the second analyte binding partner 103 conjugated to a first detectable label 104 and is preferably mixed with a second control binding partner 105 conjugated to a second detectable label 106, which serves as a control.

While FIG. 14 shows the different reagents in certain locations on the test strip or the sample compressor 30, other locations for each of the first analyte binding partner 102 conjugated to a second test zone binding partner 101, the binding partner 107 for the second analyte binding partner 103, the second analyte binding partner conjugated to the first detectable label 104, and the second control binding partner 105 conjugated to the second detectable label 106 on the test strip and/or on the pad 33 of the sample compressor 30 are also possible. Other embodiments do not require a sample compressor 30. In these embodiments, the reagents 101, 102, 103, 104, 105, 106, 107, and 108 will be located in various locations, preferably upstream of the test zone 45, on the test strip.

Figure 15A:
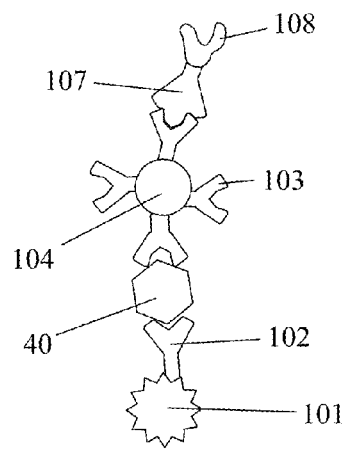
FIG. 15A shows a stack that forms in an embodiment of the present invention.
Figure 15B:
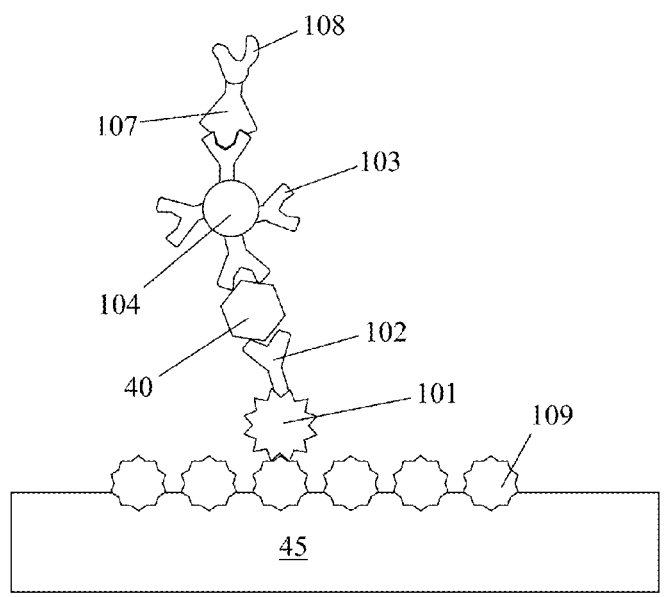
FIG. 15B shows the stack of FIG. 15A immobilized in the test zone.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 15A and 15B show the different complexes that form between the test reagents and the analyte. If the analyte 40 is present in the sample, it complexes with the first analyte binding partner 102 and the second analyte binding partner 103, which complexes with the binding partner 107 conjugated with the enzyme 108.

Figure 15C:
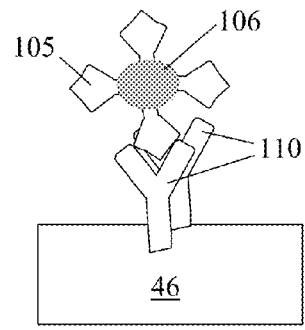
FIG. 15C shows a complex that forms in the control zone.

If the analyte 40 is not present in the sample, the second analyte binding partner 103 still complexes with the binding partner 107 conjugated with the enzyme 108, but they do not complex with the sample or the first analyte binding partner 102. The second test zone binding partner 101 will bind to the first test zone binding partner 109 in the test zone 45, regardless of whether or not the analyte 40 is present in the sample. However, if there is no analyte present, nothing will be visible at the test line. The result is visually read at approximately ten minutes. If a visible test line forms along with a visible control line, the result indicates high levels of analyte in the sample. If, at the end of 10 minutes, there is no visible line at the test line, then one drop of a substrate for the enzyme is added at the test line. If addition of the enzyme substrate results in a visible signal, the result indicates a weak positive sample. A visible line at the control line indicates that the second control binding partner 105 conjugated to the second detectable label 106 has bound to the first control binding partner 110 in the control zone 46 and that the test has run correctly. FIG. 15C shows the complex that forms in the control zone.

As an example, a Herpes Simplex Virus (HSV) detector includes the following sections, as shown in FIG. 14. The control zone 46 includes immobilized rabbit anti chicken IgY antibody 110. The test zone 45 includes immobilized NeutrAvidin 109 on the nitrocellulose membrane. Biotinylated 101 polyclonal anti HSV-1 and/or HSV-2 102 is dried onto the sample application zone 44. While not shown in this figure, the anti HSV-1/HSV-2 102 could alternatively be dried upstream or downstream of the sample application zone 44. Rabbit anti-mouse IgG (H&L) 107 conjugated to horseradish peroxidase (HRP) 108 is dried upstream of the sample application zone 44. Alternatively, the rabbit-anti-mouse IgG 107 conjugated to horseradish peroxidase 108 could overlap the sample application zone 44 or be located downstream of the sample application zone 44. The pad 33 on the sample compressor 30 is preferably embedded with mouse monoclonal anti gD 1&2 103 (monoclonal antibodies directed against glycoprotein D of herpes simplex virus) conjugated to colloidal gold 104 and mixed with chicken IgY 105 conjugated to blue dyed latex beads 106, which serves as a control.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 15A and 15B show the different complexes that form between the test reagents and the analyte. If HSV (the analyte 40) is present in the sample, it complexes with the biotinylated 101 polyclonal anti HSV1/2 102 and the mouse monoclonal anti gD1&2 103 conjugated to colloidal gold 104, which complexes with the rabbit anti-mouse IgG 107 conjugated with HRP 108.

If HSV is not present in the sample, the mouse monoclonal anti gD1&2 103 conjugated to colloidal gold 104 still complexes with the rabbit anti-mouse IgG 107 conjugated with HRP 108, but they do not complex with the sample or the biotinylated 101 polyclonal anti HSV1/2 102. The biotinylated 101 polyclonal anti HSV1/2 102 will bind to neutravidin 109 in the test zone 45, regardless of whether or not HSV is present in the sample. However, if there is no HSV present, the biotinylated 101 polyclonal anti HSV 1/2 102 will not be visible at the test line. The result is visually read at approximately ten minutes. If a visible red test line forms along with the blue control line, the result indicates high levels of HSV in the sample. If, at the end of 10 minutes, there is no visible red line at the test line, then one drop of the enzyme substrate TMBM (or another substrate for horseradish peroxidase) is added at the test line. If addition of the TMBM results in a blue/purple test line, the result indicates a weak positive sample. A blue line at the control line indicates that the chicken IgY 105 conjugated to the blue dyed latex beads 106 has bound to the rabbit anti-chicken IgY 110 in the control zone 46 and that the test has run correctly. FIG. 15C shows the complex that forms in the control zone.

In this embodiment, the point of care test becomes enzyme-linked and the amplification depends on the amount of enzyme and substrate, and increases with time. This does not happen in visually tagged conjugates to nanoparticles like colloidal gold or microspheres like latex beads. In addition, the test line result is not due to any antigen-antibody immunoassay, but a binding assay between a ligand and a receptor such as neutravidin and biotin. The binding at the test line is not due to immunological binding but chemical binding. Thus it is not an enzyme-linked immunoassay (ELISA or EIA). Instead, it is an enzyme-linked chromofiltography, or direct multiplanar enzyme chromofiltography when used with a sample compressor. Even with an additional step of adding the enzyme substrate to the test line, the test is still simple to perform.

Figure 16:
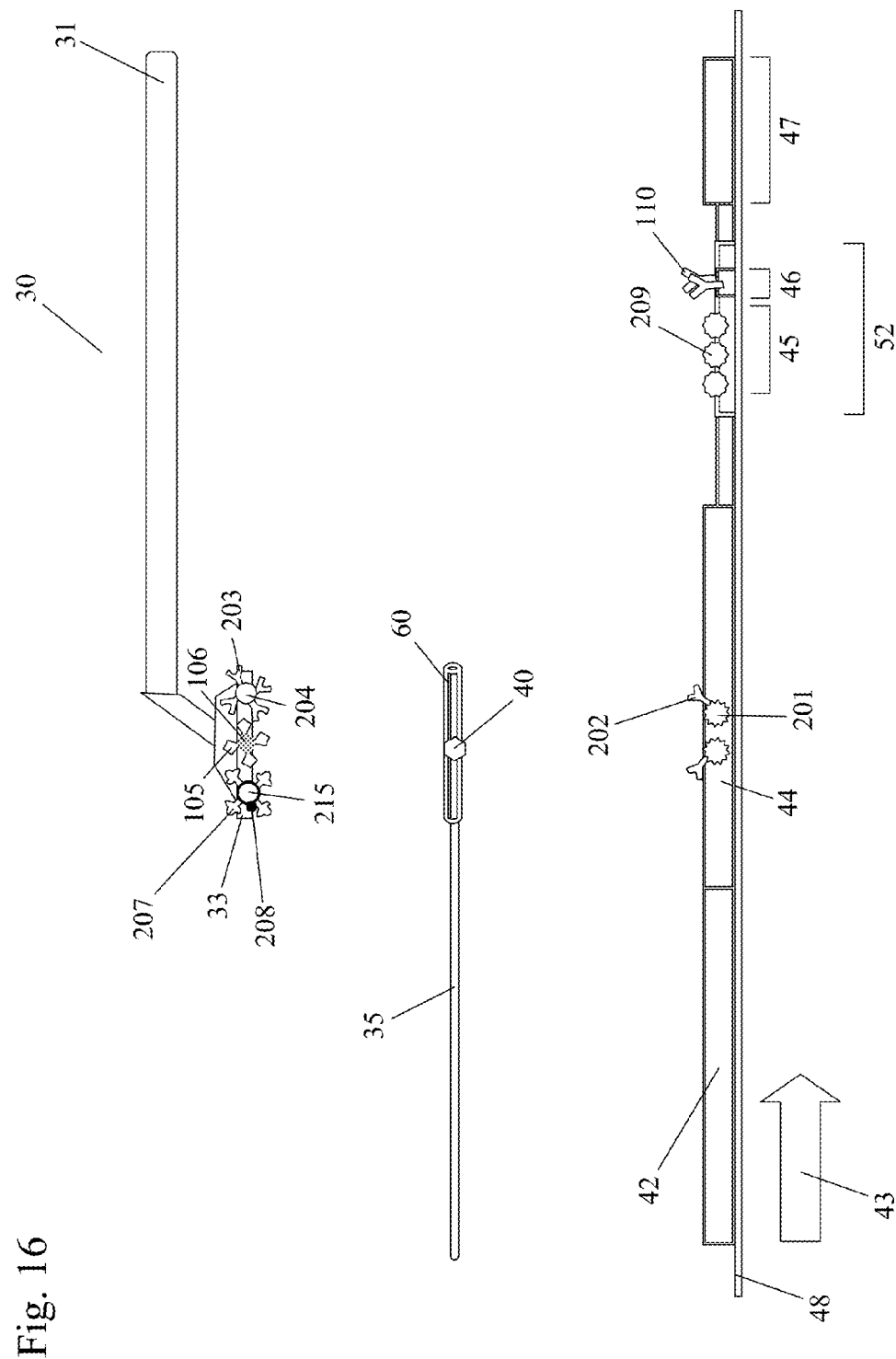
FIG. 16 shows a lateral flow device in another embodiment of the present invention.
Figure 17A:
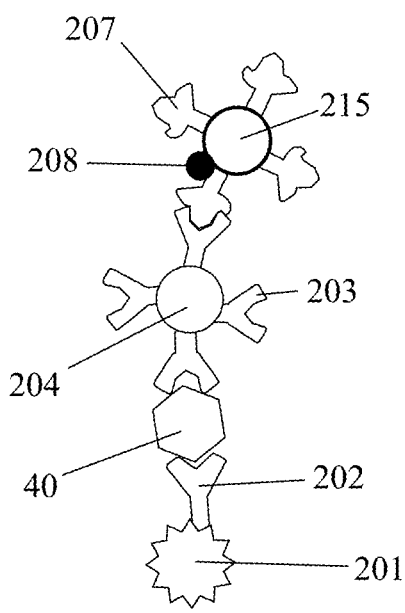
FIG. 17A shows a stack that forms in an embodiment of the present invention.
Figure 17B:
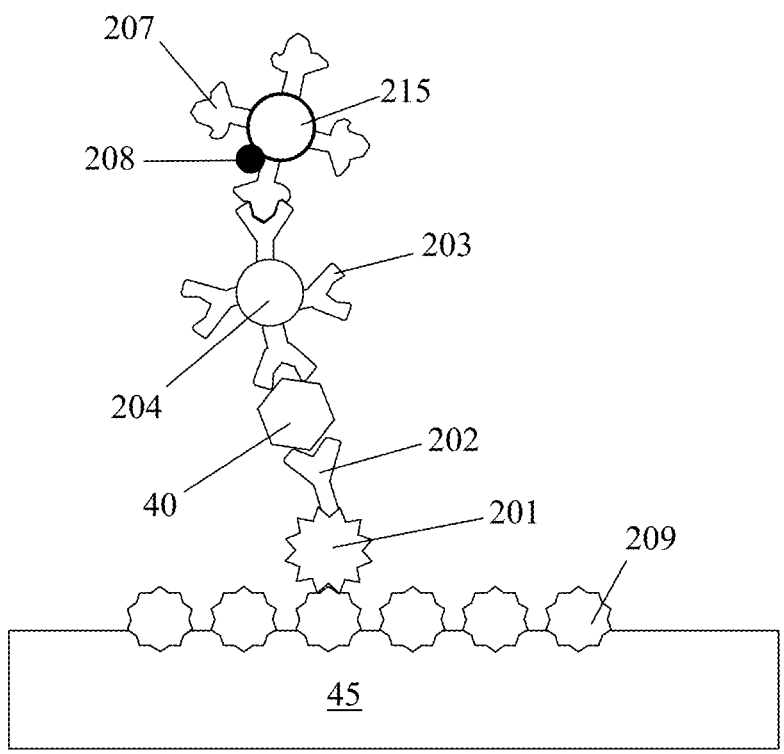
FIG. 17B shows the stack of FIG. 17A immobilized in the test zone.

In an alternative stacking embodiment, shown in FIGS. 16, 17A, and 17B, an enzyme is physically bound to the detectable label on both the conjugate and the stacking moiety. In one example, the enzyme coats visibly detectable beads (for example, red latex beads) and is conjugated to a rabbit anti-mouse antibody. While horseradish peroxidase is often used to amplify a weak signal, other enzymes that enhance weak signals could alternatively be used including, but not limited to, alkaline phosphatase, catalase, urease, and glucose oxidase. Similarly, other antibodies that bind to the conjugate or an intermediary could alternatively be used. There are no nanoparticles or microspheres in this embodiment. Instead, this embodiment includes a "soluble" form of the conjugate. The location where this enzyme conjugate is dried can vary; it can be upstream, downstream, or overlapping the sample application zone. In embodiments with a sample compressor, the enzyme conjugate could alternatively be on the sample compressor. The enzyme conjugate is preferably dried on the test strip, but not immobilized. It can be located alone or in combination with other components that form the "sandwich" with the antibody, which is preferably biotinylated.

FIG. 16 shows an embodiment of a detector with an enzyme physically bound to the detectable label on both the conjugate and the stacking moiety. The control zone 46 includes an immobilized first control binding partner 110, similar to the detector shown in FIG. 14. The test zone 45 includes an immobilized first test zone binding partner 209 on a membrane. A first analyte binding partner 202 conjugated to a second test zone binding partner 201 is dried or otherwise incorporated (e.g., lyophilized) into the sample application zone 44. While not shown in this figure, the first analyte binding partner 202 could alternatively be located upstream or downstream of the sample application zone 44.

A binding partner 207 for a second analyte binding partner 203, which is conjugated to an enzyme 208 and conjugated to a detectable label 215 (which is also conjugated to the enzyme 208), is preferably embedded into the pad 33 the sample compressor 30. In other embodiments, there is only a binding partner 207 for the second analyte binding partner 203 conjugated to a detectable label 215, and the detectable label is also conjugated to the enzyme 208. In some embodiments, the enzyme 208 is conjugated to the detectable label 215 by coating the detectable label 215. In some embodiments, the binding partner 207 conjugated to the enzyme 208 plus the binding partner 207 conjugated to the detectable label 215 (which is also conjugated to the enzyme 208) could be located on the test strip, overlapping the sample application zone 44 or being located downstream or upstream of the sample application zone 44. The pad 33 on the sample compressor 30 is preferably also embedded with the second analyte binding partner 203 conjugated to a detectable label 204 coated with the enzyme 208, which is preferably mixed with a second control binding partner 105 conjugated to a detectable label 106 (shown in FIG. 14), which serves as a control.

While FIG. 16 shows the different reagents in certain locations on the test strip or the sample compressor 30, other locations for each of the first analyte binding partner 202 conjugated to the second test zone binding partner 201, the binding partner 207 conjugated to the enzyme 208 plus the binding partner 207 conjugated to the detectable label 215 coated with the enzyme, and the second control binding partner 105 conjugated to the detectable label 106, on the test strip and/or on the pad 33 of the sample compressor 30 are also possible. Other embodiments do not require a sample compressor 30. In these embodiments, the reagents 201, 202, 203, 204, 105, 106, 207, 208, and 215 will be located in various locations, preferably upstream of the test zone 45, on the test strip.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 17A and 17B show the different complexes that form between the test reagents and the analyte. If the analyte 40 is present in the sample, it complexes with the first analyte binding partner 202 and the second analyte binding partner 203. The second analyte binding partner also complexes with the binding partner 207.

If the analyte 40 is not present in the sample, the second analyte binding partner 203 still complexes with the binding partner 207, but they do not complex with the sample or the first analyte binding partner 202. The second test zone binding partner 201 will bind to the first test zone binding partner 209 in the test zone 45, regardless of whether or not the analyte 40 is present in the sample. However, if there is no analyte 40 present, the second test zone binding partner 201 conjugated to the first analyte binding partner 202 and complexed with the first test zone binding partner 209 will not be visible at the test line. The result is visually read at approximately ten minutes. If a visible test line forms along with a visible control line, the result indicates high levels of analyte in the sample. If, at the end of 10 minutes, there is no visible line at the test line, then one drop of the enzyme substrate is added at the test line. If addition of the enzyme substrate results in a visible test line, the result indicates a weak positive sample. A visible line at the control line indicates that the second control binding partner 105 has bound to the first control binding partner 110 in the control zone 46 and that the test has run correctly. The control line complex is shown in FIG. 15C.

In this embodiment, the enzyme is physically bound to the detectable label (for example, latex beads) and moves with the detectable label. Thus, specificity and background issues are improved. At high levels of antigen, a positive result is easily visibly detectable by a visible line. At very low levels, the enzyme substrate is added to the results window to get an enzyme-amplified color reaction. By depositing many of the reagents, including the binding partner 207, which includes the enzyme 208 and the detectable label 215, on the sample compressor, these reagents are not on the strip. In some preferred embodiments, the second analyte binding partner 203 can be premixed with the binding partner 207 (with or without the enzyme labeled binding partner) and be embedded in the sample compressor pad. In these embodiments, the test strip includes the second test zone binding partner 202, which binds to the first test zone binding partner 209. This makes the test strip into a binding assay and not an immunoassay.

As an example, a Herpes Simplex Virus (HSV) detector includes the following sections, as shown in FIG. 16. The control zone 46 includes immobilized rabbit anti chicken IgY antibody 110, similar to the detector shown in FIG. 14. The test zone 45 includes immobilized NeutrAvidin 209 on the nitrocellulose membrane. Biotinylated 201 polyclonal anti HSV-1 and/or HSV-2 202 is dried onto the sample application zone 44. While not shown in this figure, the anti HSV-1/HSV-2 202 could alternatively be dried upstream or downstream of the sample application zone 44. Rabbit anti-mouse IgG (H&L) 207 conjugated to horseradish peroxidase (HRP) 208 plus rabbit anti-mouse IgG 207 conjugated to red latex beads 215 coated with horseradish peroxidase and is preferably embedded into the pad 33 the sample compressor 30. In other embodiments, there is only rabbit anti-mouse IgG 207 conjugated to red latex beads 215 coated with horseradish peroxidase. Alternatively, the rabbit-anti-mouse IgG 207 conjugated to horseradish peroxidase 208 plus rabbit anti-mouse IgG 207 conjugated to red latex beads 215 coated with horseradish peroxidase could be located on the test strip, overlapping the sample application zone 44 or being located downstream or upstream of the sample application zone 44. The pad 33 on the sample compressor 30 is preferably also embedded with mouse monoclonal anti gD 1&2 203 (monoclonal antibodies directed against glycoprotein D of herpes simplex virus) conjugated to red latex beads 204 coated with horseradish peroxidase and mixed with chicken IgY 105 conjugated to blue dyed latex beads 106 (shown in FIG. 14), which serves as a control.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 17A and 17B show the different complexes that form between the test reagents and the analyte. If HSV (the analyte 40) is present in the sample, it complexes with the biotinylated 201 polyclonal anti HSV1/2 202 and the mouse monoclonal anti gD1&2 203 conjugated to red latex beads 204, which complexes with the rabbit anti-mouse IgG 207 conjugated with HRP 208 and the rabbit anti-mouse IgG 207 conjugated to red latex beads 215 coated with horseradish peroxidase.

If HSV is not present in the sample, the mouse monoclonal anti gD1&2 203 conjugated to the red latex beads 204 still complexes with the rabbit anti-mouse IgG 207, but they do not complex with the sample or the biotinylated 201 polyclonal anti HSV1/2 202. The biotinylated 201 polyclonal anti HSV1/2 202 will bind to NeutrAvidin 209 in the test zone 45, regardless of whether or not HSV is present in the sample. However, if there is no HSV present, the biotinylated 201 polyclonal anti HSV 1/2 202 will not be visual at the test line. The result is visually read at approximately ten minutes. If a visible red test line forms along with the blue control line, the result indicates high levels of HSV in the sample. If, at the end of 10 minutes, there is no visible red line at the test line, then one drop of the enzyme substrate TMBM (or another substrate for horseradish peroxidase) is added at the test line. If addition of the TMBM results in a blue/purple test line, the result indicates a weak positive sample. A blue line at the control line indicates that the chicken IgY 105 conjugated to the blue dyed latex beads 106 has bound to the rabbit anti-chicken IgY 110 in the control zone 46 and that the test has run correctly. The control line complex is shown in FIG. 15C.

In this example, rabbit anti mouse antibody is conjugated to the enzyme, which is also conjugated to the red latex beads, and additional rabbit anti-mouse antibody is conjugated directly to the same beads. The enzyme is physically bound to the beads and moves with the beads. Thus, specificity and background issues are improved. At high levels of antigen, a positive result is easily visibly detectable by a red line. At very low levels, the enzyme substrate is added to the results window to get an enzyme-amplified color reaction.

By depositing the rabbit anti mouse antibody conjugated to the red beads (along with the enzyme conjugate on the same bead) on the sample compressor, these reagents are not on the strip. In some preferred embodiments, the free mouse monoclonal anti gD 1&2 can be premixed with the rabbit anti mouse (with or without the enzyme labeled rabbit anti mouse) and be embedded in the sample compressor pad. In these embodiments, the test strip includes biotin which binds to neutravidin. This makes the test strip into a binding assay and not an immunoassay.

Figure 18:
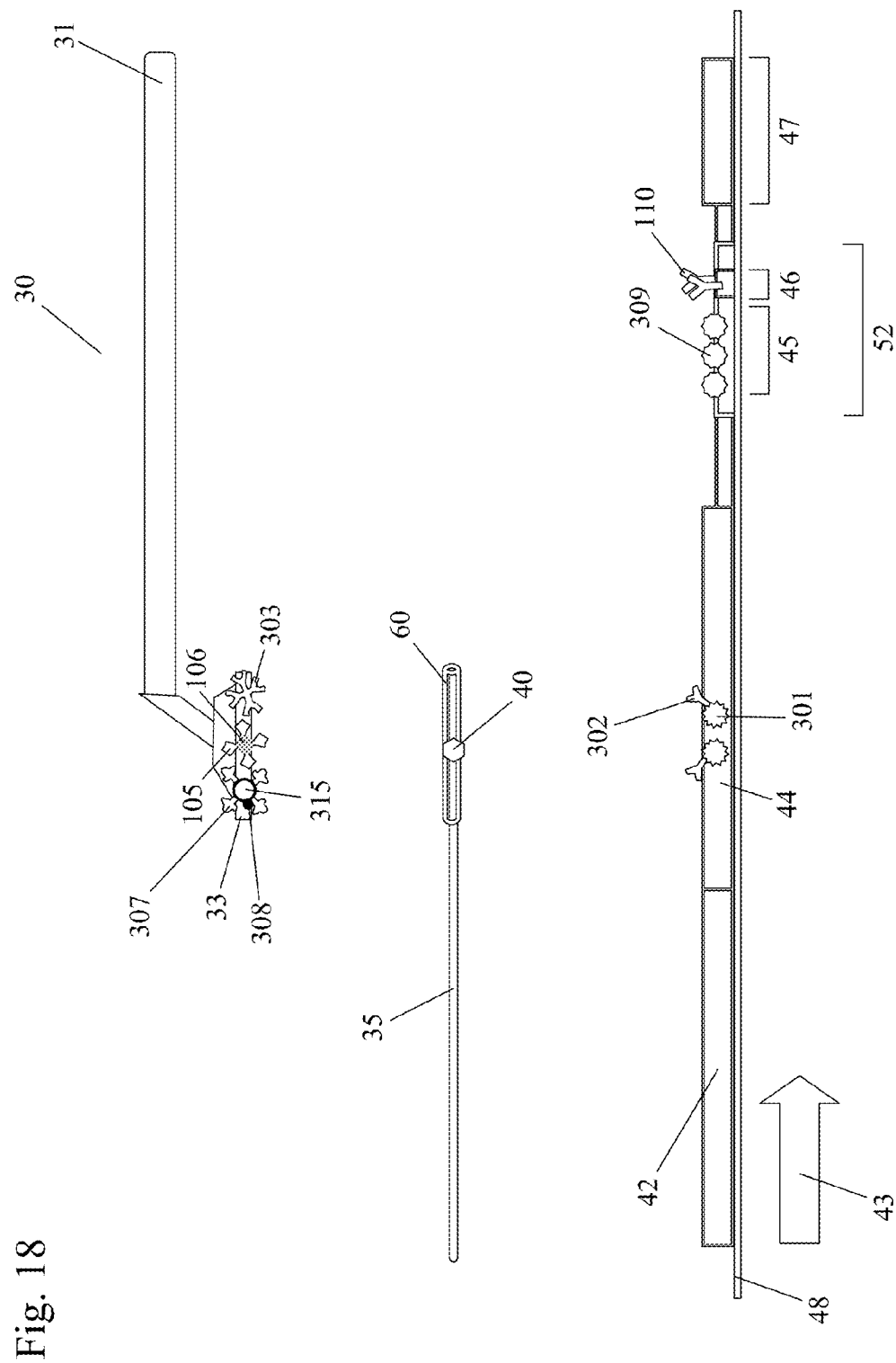
FIG. 18 shows a lateral flow device in another embodiment of the present invention.
Figure 19A:
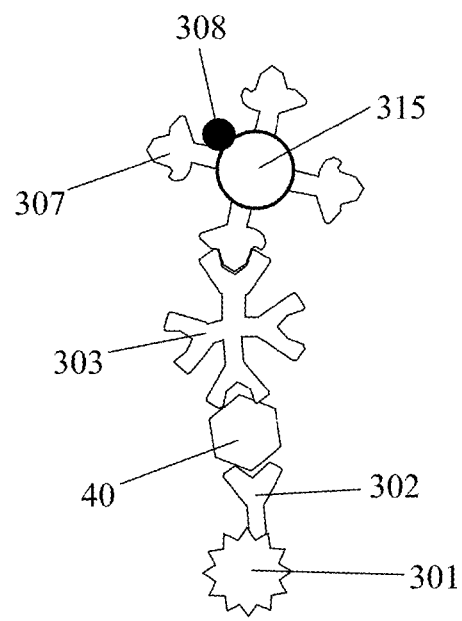
FIG. 19A shows a stack that forms in an embodiment of the present invention.
Figure 19B:
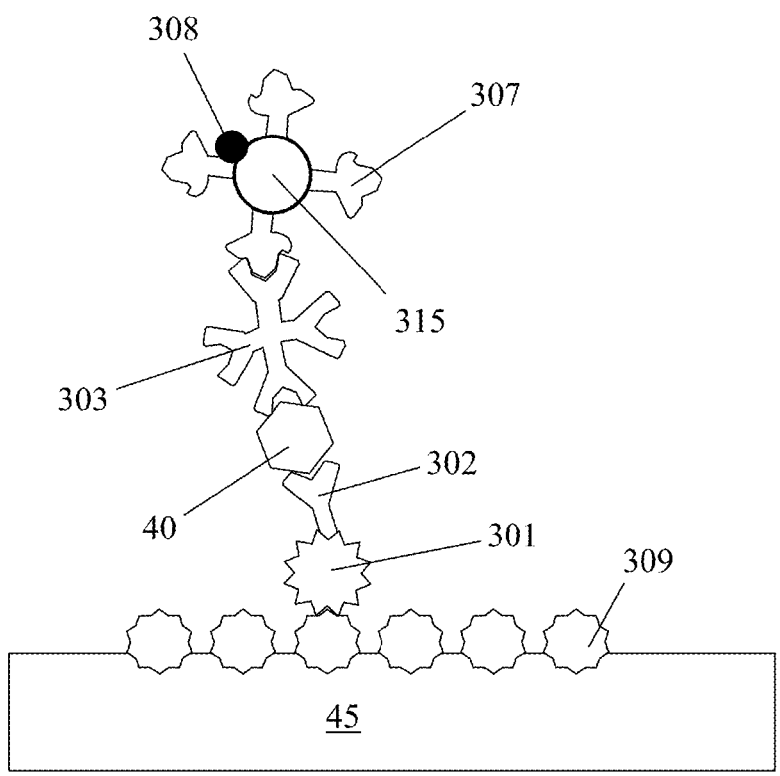
FIG. 19B shows the stack of FIG. 19A immobilized in the test zone.

FIGS. 18, 19A, and 19B show another stacking embodiment of the present invention. In this embodiment, an enzyme is conjugated/physically bound to a detectable label on the stacking moiety and the conjugate that binds to the analyte does not include a detectable label. This embodiment further increases specificity. In one example, the enzyme coats visibly detectable beads (for example, red latex beads) and is conjugated to a rabbit anti-mouse antibody. While horseradish peroxidase is often used to amplify a weak signal, other enzymes that enhance weak signals could alternatively be used including, but not limited to, alkaline phosphatase, catalase, urease, and glucose oxidase. Similarly, other antibodies that bind to the conjugate or an intermediary could alternatively be used. There are no nanoparticles or microspheres in this embodiment. Instead, this embodiment includes a "soluble" form of the conjugate. The location where this enzyme conjugate is dried can vary; it can be upstream, downstream, or overlapping the sample application zone. In embodiments with a sample compressor, the enzyme conjugate could alternatively be on the sample compressor. The enzyme conjugate is preferably dried on the test strip, but not immobilized. It can be located alone or in combination with other components that form the "sandwich" with the antibody (which is preferably biotinylated).

An embodiment of a detector with enzyme conjugated/ physically bound to a detectable label on the stacking moiety and a conjugate that binds to the analyte that does not include a detectable label is shown in FIG. 18. The control zone 46 includes an immobilized first control binding partner 110, similar to the detector shown in FIG. 14. The test zone 45 includes an immobilized first test zone binding partner 309 on a membrane. A first analyte binding partner 302 conjugated to a second test zone binding partner 301 is dried or otherwise incorporated (e.g., lyophilized) into the sample application zone 44. While not shown in this figure, the first analyte binding partner 302 could alternatively be located upstream or downstream of the sample application zone 44. A mixture of a binding partner 307 for the second analyte binding partner 303 conjugated to an enzyme 308 and the binding partner 307 conjugated to a detectable label 315 (for example, latex beads) coated or otherwise conjugated to the enzyme 308 is preferably embedded into the pad 33 of the sample compressor 30. In other embodiments, there is only the binding partner 307 conjugated to the detectable label 315, which is also conjugated to the enzyme 308 (for example, by the enzyme coating latex beads). While the binding partner 307 conjugated to the enzyme and the binding partner 307 conjugated to the detectable label 315 coated with the enzyme is shown on the sample compressor 30 in this figure, these components could alternatively be located on the test strip, overlapping the sample application zone 44 or being located downstream or upstream of the sample application zone 44. The pad 33 on the sample compressor 30 is preferably also embedded with a second analyte binding partner 303. Unlike in the previous embodiments, the second analyte binding partner 303 is not conjugated to a detectable label or an enzyme. In some embodiments, the second analyte binding partner 303 is preferably mixed with the second control binding partner 105 conjugated to the detectable label 106 (shown in FIG. 14), which serves as a control.

While FIG. 18 shows the different reagents in certain locations on the test strip or the sample compressor 30, other locations for each of the first analyte binding partner 302 conjugated to the second test zone binding partner 301, the mixture of the binding partner 307 for the second analyte binding partner 303 conjugated to an enzyme 308 and the binding partner 307 conjugated to a detectable label 315 coated or otherwise conjugated to the enzyme 308, the second analyte binding partner 303 and the second control binding partner 105 conjugated to a detectable label 106, on the test strip and/or on the pad 33 of the sample compressor 30 are also possible. Other embodiments do not require a sample compressor 30. In these embodiments, the reagents 301, 302, 303, 304, 105, 106, 307, 308, and 315 will be located in various locations, preferably upstream of the test zone 45, on the test strip.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 19A and 19B show the different complexes that form between the test reagents and the analyte. If the analyte 40 is present in the sample, it complexes with the first analyte binding partner 302 and the second analyte binding partner 303. The second analyte binding partner 303 also complexes with the binding partner 307.

If the analyte 40 is not present in the sample, the second analyte binding partner 303 still complexes with the binding partner 307, but they do not complex with the sample or the first analyte binding partner 302. The second test zone binding partner 301 binds to the first test zone binding partner 309 in the test zone 45, regardless of whether or not the analyte is present in the sample. However, if there is no analyte 40 present, the resulting complex will not be visible at the test line. The result is visually read at approximately ten minutes. If a visible test line forms along with the visible control line, the result indicates high levels of analyte 40 in the sample. If, at the end of 10 minutes, there is no visible line at the test line, then one drop of an enzyme substrate is added at the test line. If addition of the enzyme substrate results in a visible test line, the result indicates a weak positive sample. A visible line at the control line indicates that the second control binding partner 105 conjugated to the detectable label 106 has bound to the first control binding partner 110 in the control zone 46 and that the test has run correctly. The control line complex is shown in FIG. 15C.

In this embodiment, the binding partner 307 is conjugated to the enzyme 308, which is also conjugated to the detectable label 315 (for example, latex beads), and additional binding partner 307 is conjugated directly to the same detectable label 315. The enzyme is physically bound to the detectable label and moves with the detectable label. Thus, specificity and background issues are improved. At high levels of antigen, a positive result is easily visibly detectable by a visible line. At very low levels, the enzyme substrate is added to the results window to get an enzyme-amplified color reaction.

By depositing the binding partner 307 and its other components (308 and 315) on the sample compressor, these reagents are not on the strip. In some preferred embodiments, the second analyte binding partner 303 can be premixed with the binding partner 307 (with or without the enzyme labeled binding partner 307) and be embedded in the sample compressor pad. In these embodiments, the device includes binding partners such as biotin and avidin. This makes the test strip into a binding assay and not an immunoassay.

As an example, a Herpes Simplex Virus (HSV) detector includes the following sections, as shown in FIG. 18. The control zone 46 includes immobilized rabbit anti-chicken IgY antibody 110, similar to the detector shown in FIG. 14. The test zone 45 includes immobilized neutravidin 309 on a nitrocellulose membrane. Biotinylated 301 polyclonal anti HSV-1 and/or HSV-2 302 is dried onto the sample application zone 44. While not shown in this figure, the anti HSV-1/HSV-2 302 could alternatively be located upstream or downstream of the sample application zone. Rabbit anti-mouse IgG (H&L) 307 conjugated to horseradish peroxidase (HRP) 308 plus rabbit anti-mouse IgG 307 conjugated to red latex beads 315 coated with horseradish peroxidase is preferably embedded into the pad 33 of the sample compressor. In other embodiments, there is only rabbit anti-mouse IgG 307 conjugated to red latex beads 315 coated with horseradish peroxidase. Alternatively, the rabbit anti-mouse IgG 307 conjugated to horseradish peroxidase 308 plus rabbit anti-mouse IgG 307 conjugated to red latex beads coated with horseradish peroxidase 308 could be located on the test strip, overlapping the sample application zone 44 or being located downstream or upstream of the sample application zone 44. The pad on the sample compressor 30 is preferably also embedded with free mouse monoclonal anti gD 1&2 303. Unlike in the previous embodiments, the free mouse monoclonal antibodies 303 are not conjugated to a detectable label or an enzyme. The free mouse monoclonal antibodies 303 are preferably mixed with chicken IgY 105 conjugated to blue dyed latex beads (shown in FIG. 14), which serves as a control.

The sample is taken on a sample swab 35, which is then placed on the sample application zone 44 through the sample window 81 (in embodiments with a housing and a sample window) or just on the sample application zone 44. The sample compressor 30 is then compressed onto the sample application zone 44. The absorbent tip of the sample compressor 30 is preferably immersed in running buffer for approximately 15-30 seconds before removing the sample compressor 30. FIGS. 19A and 19B show the different complexes that form between the test reagents and the analyte. If HSV (the analyte 40) is present in the sample, it complexes with the biotinylated 301 polyclonal anti HSV1/2 302 and the mouse monoclonal anti gD1&2 303, which complexes with the rabbit anti-mouse IgG 307 conjugated with HRP 308 and the rabbit anti-mouse IgG 307 conjugated to red latex beads 315 coated with horseradish peroxidase.

If HSV is not present in the sample, the mouse monoclonal anti gD1&2 303 still complexes with the rabbit anti-mouse IgG 307, but they do not complex with the sample or the biotinylated 301 polyclonal anti HSV1/2 302. The biotinylated 301 polyclonal anti HSV1/2 202 will bind to neutravidin 309 in the test zone 45, regardless of whether or not HSV is present in the sample. However, if there is no HSV present, the biotinylated 301 polyclonal anti HSV 1/2 302 will not be visible at the test line. The result is visually read at approximately ten minutes. If a visible red test line forms along with the blue control line, the result indicates high levels of HSV in the sample. If, at the end of 10 minutes, there is no visible red line at the test line, then one drop of the enzyme substrate TMBM (or another substrate for horseradish peroxidase) is added at the test line. If addition of the TMBM results in a blue/purple test line, the result indicates a weak positive sample. A blue line at the control line indicates that the chicken IgY 105 conjugated to the blue dyed latex beads 106 has bound to the rabbit anti-chicken IgY 110 in the control zone 46 and that the test has run correctly. The control line complex is shown in FIG. 15C.

In this example, rabbit anti mouse antibody is conjugated to the enzyme, which is also conjugated to the red latex beads, and additional rabbit anti-mouse antibody is conjugated directly to the same beads. The enzyme is physically bound to the beads and moves with the beads. Thus, specificity and background issues are improved. At high levels of antigen, a positive result is easily visibly detectable by a red line. At very low levels, the enzyme substrate is added to the results window to get an enzyme-amplified color reaction.

By depositing the rabbit anti mouse antibody conjugated to the red beads (along with the enzyme conjugate on the same bead) on the sample compressor, these reagents are not on the strip. In some preferred embodiments, the free mouse monoclonal anti gD 1&2 can be premixed with the Rabbit anti mouse (with or without the enzyme labeled Rabbit anti mouse) and be embedded in the sample compressor pad. In these embodiments, the device includes binding partners such as biotin and avidin. This makes the test strip into a binding assay and not an immunoassay.

In some preferred embodiments, the nitrocellulose is "blocked" with blockers, which increases the specificity of the reaction. Some examples for blockers include, but are not limited to, casein, and Bovine Serum Albumin (BSA). Whenever one blocks the nitrocellulose membrane, the inherent charge of the nitrocellulose is neutralized and thus, no additional protein can bind to the blocked membrane. In addition, the chromatographic structure is changed and the flow is more like a gliding or sliding flow instead of traditional chromatography. The result is a unique chromofiltography process.

Figure 21A:
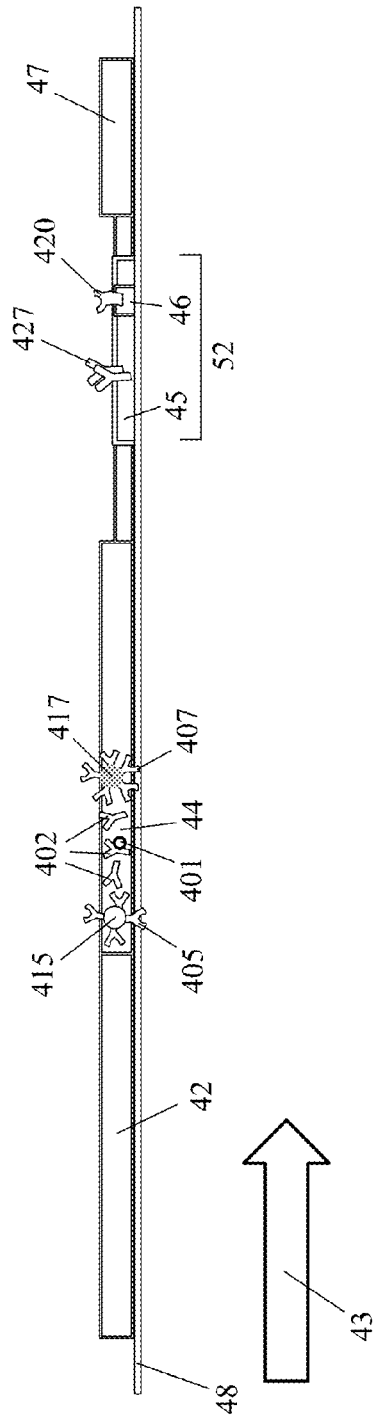
FIG. 21A shows another embodiment of a lateral flow test strip with enhancing elements.

FIG. 21A shows another embodiment of a lateral flow test strip with enhancing elements. This embodiment preferably includes a labeled binding partner 407 that is specific for a species instead of an analyte 40. As an example, when the binding partner 402 for the analyte is a mouse antibody, the labeled species specific binding partner 407 is an anti-mouse antibody. As another example, when the binding partner 402 for the analyte is a rabbit antibody, the labeled species specific binding partner 407 is an anti-rabbit antibody. Those skilled in the art would understand that any species specific binding partner 407, or other binding partner not specific for the analyte 40 but specific for a binding partner 402 for the analyte, could be used in this embodiment. Those skilled in the art would also know how to choose species to minimize cross-reactions.

The sample application zone 44 includes a first binding partner 402 for the analyte 40. Note that the first binding partner 402 does not include a detectable label. In this embodiment, some of the first binding partner 402 is preferably tagged 401 and a binding partner 409 for the tag 401 is preferably labeled with a detectable label. In preferred embodiments, the amount of the first binding partner 402 that is tagged 401 is from 1-10% of the total amount of the first binding partner 402 in the test.

The sample application zone 44 also includes a labeled species specific binding partner 407 (conjugated to a detectable label 417) that binds to the first binding partner 402 due to the species of the first binding partner 402. The sample application zone 44 also preferably includes a labeled 415 control binding partner 405 While the first binding partner 402 for the analyte 40, the conjugate including a visible label 417 and a species specific binding partner 407, and the control conjugate 405 conjugated to a visible label 415 are shown in the sample application zone 44 in this figure, any combination of these elements may be located in other locations on the test strip (upstream, downstream, or overlapping the sample application zone) or on a sample compressor 30, as described in earlier embodiments.

The test zone 45 includes an immobilized second binding partner 427 to the analyte 40. The control zone 46 includes an immobilized binding partner 420 for the control binding partner 405. The test zone 45 and the control zone 46 are preferably located on a nitrocellulose membrane.

When a sample including analyte 40 is added to the test strip, the first binding partner 402 binds to the analyte 40 and forms a "half sandwich". This preferably occurs without flow on the test strip. When running buffer is applied, it mobilizes the "half sandwich". The running buffer also mobilizes the species specific binding partner 407. During flow, the species specific binding partner 407 interacts with and binds to the first binding partner 402 in the half sandwich. Due to multiple binding sites on the first binding partner 402, there is an aggregation or stacking effect that enhances the detection of the analyte 40. In the test zone 45, the analyte 40, which is now part of an aggregate or stacked complex, binds to the immobilized second binding partner 427 to form the full sandwich. The result is an enhanced visible signal formed in the test zone 45. Binding between the control binding partner 405 and the immobilized control binding partner 420 results in a detectable signal 415.

In the presence of the analyte 40, the detectable signal 417 conjugated to the species specific binding partner 407 is part of the complex and should be visible. If a visible test line is "read" by the user, the test is recorded as a positive result for the presence of the analyte 40. If the test line is not visible or equivocal, then one or more drops of a fluid including a tag binding partner 409 for the tag 401 conjugated to a detectable label (for example, colloidal gold or latex beads) is added in the test zone 45. The tag binding partner 409 instantly binds to the tag 401 on the first binding partner 402. This greatly enhances the visibility of the test line in the presence of the analyte 40. In the absence of the analyte, the tag binding partner 409 dissipates and no test line is visible.

Figure 21B:
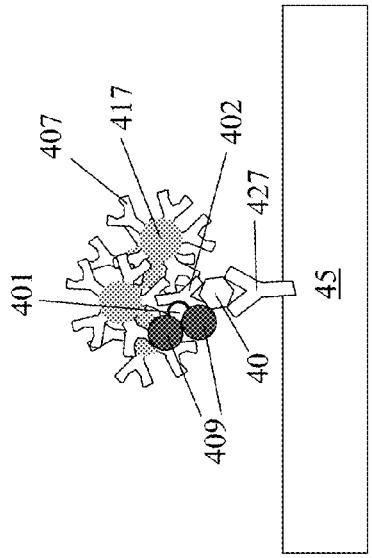
FIG. 21B shows the stacked complex at the test line in the presence of analyte.
Figure 21C:
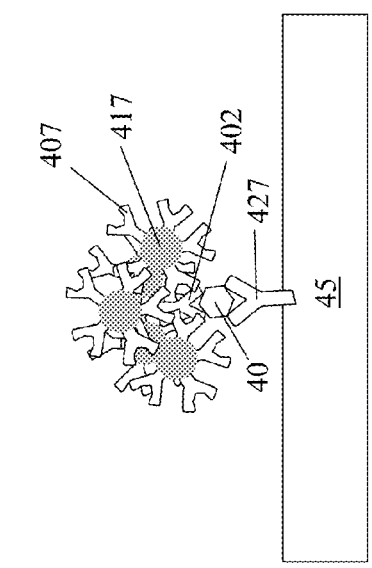
FIG. 21C shows a stacked complex at the test line with additional enhancing elements.

FIG. 21B shows a stacked complex at the test line when analyte 40 is present in the sample. FIG. 21C shows the stacked complex with the addition of the tags 401 and 409.

In an example of the embodiment shown in FIGS. 21A through 21C for detecting Herpes Simplex Virus (HSV), the sample application zone 44 includes free mouse HSV gD 1&2 402 (which binds to HSV), as well as some biotinylated 401 mouse HSV gD1&2 402. In a preferred embodiment, approximately 1-10% of the free HSV gD1&2 402 is biotinylated 401.

The sample application zone 44 also includes rabbit anti-mouse antibody 407 conjugated to red latex beads 417 and a control chicken IgY antibody 405 conjugated to blue latex beads 415. Note that the rabbit anti-mouse antibody 407 is not specific to an analyte 40. Instead, it binds specifically to the mouse HSV gD1&2 antibody 402. As discussed above, any of the HSV gD1&2 402, the biotinylated 401 HSV gD1&2 402, the rabbit anti-mouse antibody conjugated to the red latex beads, the chicken IgY antibody conjugated to blue latex beads, or any combination of these elements, may alternatively be upstream, downstream, or overlapping the sample application zone 44, or included on a sample compressor 30 in embodiments where a sample compressor 30 is used. The test zone 45 includes immobilized rabbit anti-HSV 427, which binds to the HSV analyte 40 when present in the sample. The control zone 46 includes immobilized rabbit anti-chicken/rabbit IgG 420. The test zone 45 and the control zone 46 are preferably located on a nitrocellulose membrane.

When a sample including analyte 40 is added to the test strip, the HSV gD1&2 402 binds to the HSV analyte 40 and forms a "half sandwich". This occurs without flow on the test strip. When running buffer is applied, it mobilizes the "half sandwich". The running buffer also mobilizes the rabbit anti-mouse antibody 407. During flow, the rabbit anti-mouse antibody 407 interacts with and binds to the HSV gD1&2 402 antibody in the half sandwich. Due to multiple binding sites on the mouse antibody 402, there is an aggregation or stacking effect that enhances the detection of the analyte 40. In the test zone 45, the aggregate or stacked complex analyte 40, which is now part of an aggregate or stacked complex, binds to the immobilized rabbit anti-HSV 427 to form the full sandwich. The result is an enhanced visible signal forming in the test zone 45. Binding occurs between the control conjugate chicken IgY 405 and the immobilized rabbit anti-chicken/rabbit IgG 420, resulting in a blue detectable label 415.

In the presence of the analyte 40, the red latex beads 417 conjugated to the rabbit anti-mouse antibody 407 are part of the complex and should be visible. If a visible test line is "read" by the user, the test is recorded as a positive result for the presence of the analyte 40. If the test line is not visible or equivocal, then a drop of avidin, Neutravidin, or streptavidin conjugated 409 to colloidal gold or latex beads is added in the test zone 45. The avidin, neutravidin, or streptavidin conjugate 409 instantly binds to the biotin 401 on the HSV gD1&2 antibody 402. This greatly enhances the visibility of the test line in the presence of the analyte 40. In the absence of the analyte, the avidin, streptavidin, or neutravidin conjugate 409 dissipates and no test line is visible.

In some embodiments, instead of a nitrocellulose membrane, one can use membranes such as nylon or polyester which are neutral. In these embodiments, the proteins such as neutravidin, antibodies and antigens are not immobilized directly. They are instead, conjugated to microspheres which are "deposited" into the membrane and are held in the crevices. While using a neutral membrane is shown with respect to this particular embodiment, neutral membranes and microspheres deposited onto those membranes could alternatively be used in other embodiments of the present invention.

Figure 13:
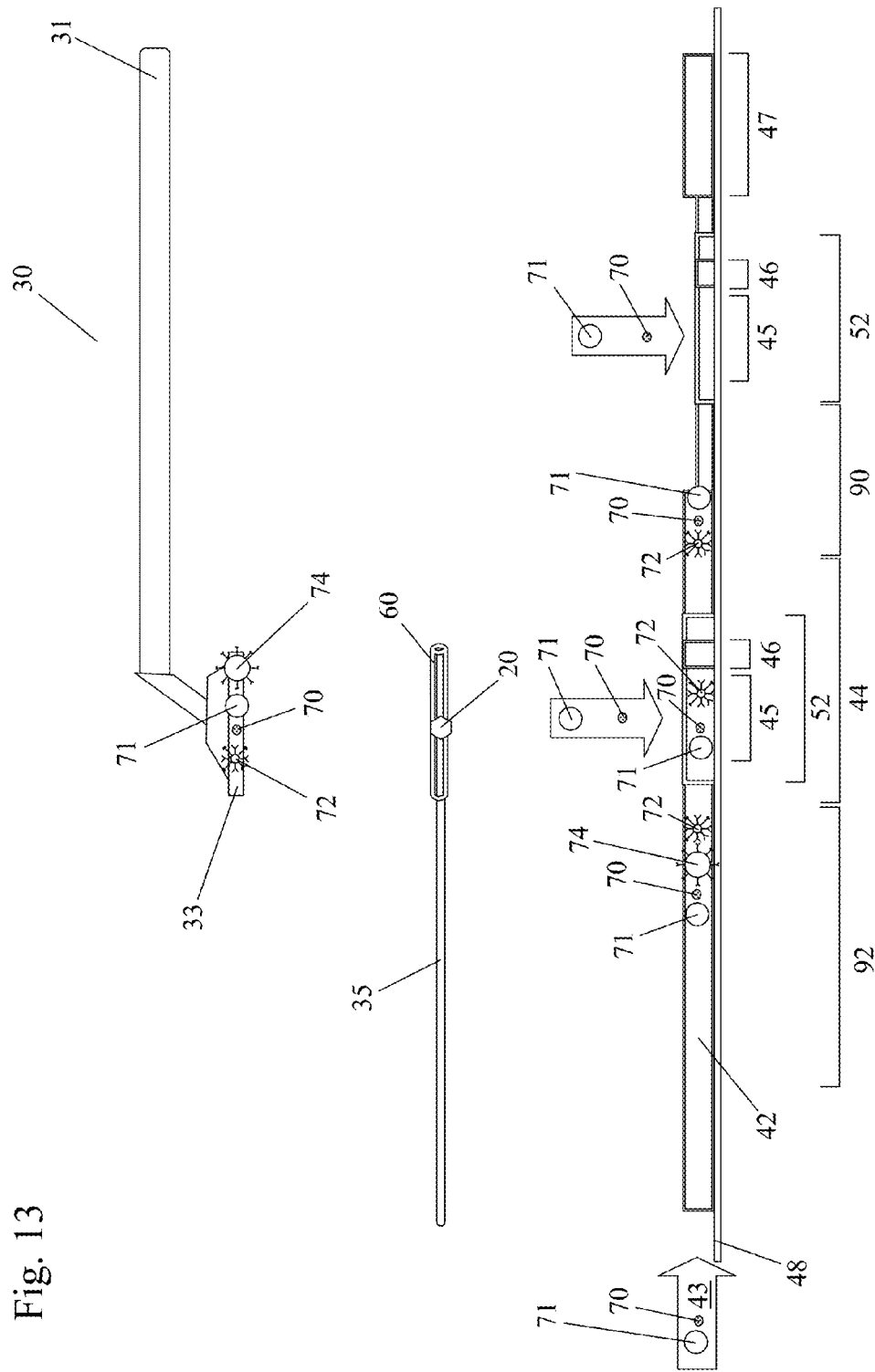
FIG. 13 shows a schematic exploded view of a lateral flow device with signal enhancement elements in embodiments of the present invention.

FIG. 13 shows some preferred locations of signal enhancement materials for both silver enhancement and stacking in embodiments of lateral flow devices of the present invention. FIG. 13 schematically shows two options for the location of the detection zone, and only the elements specific to the signal enhancement are shown in the figure.

In embodiments with silver enhancement, the silver salt 70 is preferably located in a zone 90 between the sample application zone 44 and the test zone 45 to allow at least part of the sandwich to form before silver salt binding. Alternatively, the silver salt 70 may be placed on the pad 33 of the sample compressor 30, in the sample application zone 44, in a zone 92 upstream of the sample application zone 44, in the running buffer 43, or directly on the test zone 45 after the assay has been run. In some embodiments, the silver developer 71 is also located in the zone 90 between the sample application zone and the test zone. In other embodiments, the silver developer 71 is located in the zone 92 upstream of the sample application zone 44, in the running buffer 43, on the pad 33 of the sample compressor 30, or directly on the test zone 45 after the assay has been run.

In embodiments with stacking, the first conjugate 72 may be located on the pad 33 of the sample compressor 30, in the sample application zone 44, in a zone 92 upstream of the sample application zone 44, or in a zone 90 downstream from the sample application zone. Alternatively, the first conjugate 72 may be pre-mixed with the sample prior to application to the sample application zone; in this embodiment, the half sandwich is formed outside of the assay device. The second conjugate 74 is preferably located in a zone 92 upstream from the sample application zone. Alternatively, the second conjugate 74 may be located on the pad 33 of the sample compressor 30. Alternatively, the second conjugate 74 may be in a location where it can be delayed from reaching the first conjugate 72, including, but not limited to, upstream of the sample application zone, upstream of the conjugate, or added at a time after the assay has begun, such as in the running buffer or directly at the test zone. Although not preferred, either or both of the first conjugate 72 or the second conjugate 74 could alternatively be located in the running buffer 43 (not shown).

Although the methods and devices are described herein as sandwich assays, methods and devices of the present invention may equally be used in competitive assays. In these competitive assays, the conjugate preferably includes an analyte or an analyte analog, rather than a binding partner of the analyte, bound to a label, or, alternatively, the second binding partner is replaced with analyte or analyte analog. A positive test result is then indicated by the lack of the presence of the label in the test zone of the test strip.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A lateral flow device for detecting a target analyte in a sample comprising:
   a sample compressor comprising a pad with a first mobile control binding partner and a first analyte binding partner on the pad, wherein the first analyte binding partner binds the target analyte;
   a lateral flow chromatographic test strip comprising a control zone comprising a second control binding partner immobilized in the control zone, wherein the first mobile control binding partner is a binding partner for the second control binding partner and a positive result in the control zone indicates that an assay on the lateral flow device has been run correctly;
   wherein the first mobile control binding partner and the second control binding partner do not bind to the target analyte.

2. The lateral flow device of claim 1, further comprising a sample collector comprising a sample collection portion for collection of a sample.

3. The lateral flow device of claim 2, wherein the sample compressor, the sample collector, and the lateral flow chromatographic test strip form a vertical stack to apply the sample to the lateral flow chromatographic test strip by compression; and
   wherein the sample collector is located between the sample compressor and the lateral flow chromatographic test strip in the vertical stack.

4. A lateral flow device for detecting a target analyte in a sample comprising:
   a sample compressor comprising a pad;
   a lateral flow chromatographic test strip comprising a sample application zone and a test zone laterally downstream from the sample application zone;
   a conjugate comprising a first binding partner for the target analyte and a label;
   a second binding partner for the target analyte;
   a first mobile control binding partner located on the pad of the sample compressor; and
   the lateral flow chromatographic test strip further comprising a control zone comprising a second control binding partner immobilized in the control zone, wherein the first mobile control binding partner is a binding partner for the second control binding partner;
   wherein the conjugate, the second binding partner, or both the conjugate and the second binding partner are located on the pad of the sample compressor prior to use of the lateral flow device; and
   wherein the first mobile control binding partner and the second control binding partner do not bind to the target analyte.

5. The lateral flow device of claim 4, further comprising a sample collector comprising a sample collection portion for collection of the sample.

6. The lateral flow device of claim 5, wherein the sample compressor, the sample collector, and the lateral flow chromatographic test strip form a vertical stack to apply the sample to the lateral flow chromatographic test strip by compression; and wherein the sample collector is located between the sample compressor and the lateral flow chromatographic test strip in the vertical stack.

7. The lateral flow device of claim 4, wherein the conjugate is located on the pad and the second binding partner is located on an external medium.

8. The lateral flow device of claim 4, wherein the second binding partner is located on the pad and the conjugate is located on an external medium.

9. The lateral flow device of claim 4, wherein the lateral flow device is formed such that a positive result is only achieved by capture of the target analyte in the test zone through formation of a complex between the target analyte, the first binding partner, and the second binding partner.

10. The lateral flow device of claim 4, wherein the target analyte does not bind directly to an immobilized binding partner in the test zone.

11. The lateral flow device of claim 4, wherein the second binding partner comprises a tag and the test zone comprises an immobilized binding partner of the tag.

12. The lateral flow device of claim 4, further comprising a housing surrounding at least a portion of the lateral flow chromatographic test strip, wherein a rotatable portion of the housing forms the sample compressor.

13. The lateral flow device of claim 4, further comprising a housing surrounding at least a portion of the lateral flow chromatographic test strip, wherein an insertable cartridge forms the sample compressor.

14. A method of ensuring proper operation of a lateral flow device for detecting a target analyte, comprising a sample compressor comprising a pad and a first mobile control binding partner on the pad; and a lateral flow chromatographic test strip comprising a control zone comprising a second control binding partner immobilized in the control zone, wherein the first mobile control binding partner is a binding partner for the second control binding partner, comprising the step of:

a) running an assay on the lateral flow device such that the sample compressor exerts pressure to transfer the first mobile control binding partner to the lateral flow chromatographic test strip, and a positive result in the control zone indicates that the assay on the lateral flow device has been run correctly;

wherein the first mobile control binding partner and the second control binding partner do not bind to the target analyte.

15. The method of claim 1, wherein the first mobile control binding partner is chicken IgY conjugated to latex beads and the second control binding partner is immobilized rabbit anti-chicken IgY.

16. The method of claim 4, wherein the first mobile control binding partner is chicken IgY conjugated to latex beads and the second control binding partner is immobilized rabbit anti-chicken IgY.

17. The method of claim 14, wherein the first mobile control binding partner is chicken IgY conjugated to latex beads and the second control binding partner is immobilized rabbit anti-chicken IgY.

18. The device of claim 1, wherein the sample compressor further comprises a ledge portion connected to the pad, an extended portion extending from the ledge portion and a handle extending from the extended portion in a direction away from the pad.

* * * * *